US009006258B2

(12) United States Patent
Fienberg et al.

(10) Patent No.: US 9,006,258 B2
(45) Date of Patent: Apr. 14, 2015

(54) METHOD OF TREATING FEMALE SEXUAL DYSFUNCTION WITH A PDE1 INHIBITOR

(75) Inventors: Allen A. Fienberg, New York, NY (US); Sharon Mates, New York, NY (US); Lawrence P. Wennogle, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 817 days.

(21) Appl. No.: 12/517,945

(22) PCT Filed: Dec. 5, 2007

(86) PCT No.: PCT/US2007/024866
§ 371 (c)(1),
(2), (4) Date: Jun. 5, 2009

(87) PCT Pub. No.: WO2008/070095
PCT Pub. Date: Jun. 12, 2008

(65) Prior Publication Data
US 2010/0323997 A1 Dec. 23, 2010

Related U.S. Application Data

(60) Provisional application No. 60/873,104, filed on Dec. 5, 2006.

(51) Int. Cl.
| | | |
|---|---|---|
| A01N 43/54 | (2006.01) |
| A61K 31/505 | (2006.01) |
| A01N 43/52 | (2006.01) |
| A61K 31/415 | (2006.01) |
| A01N 43/56 | (2006.01) |
| C07D 491/00 | (2006.01) |
| C07D 239/70 | (2006.01) |
| A61K 31/495 | (2006.01) |
| A61K 31/00 | (2006.01) |
| A61K 31/519 | (2006.01) |
| A61K 31/565 | (2006.01) |
| A61K 31/57 | (2006.01) |

(52) U.S. Cl.
CPC .............. *A61K 31/495* (2013.01); *A61K 31/00* (2013.01); *A61K 31/519* (2013.01); *A61K 31/565* (2013.01); *A61K 31/57* (2013.01)

(58) Field of Classification Search
USPC .......... 514/267, 273, 393, 405; 544/247, 251, 544/252
See application file for complete search history.

(56) References Cited

U.S. PATENT DOCUMENTS

| | | | |
|---|---|---|---|
| 4,666,908 A | 5/1987 | Hamilton | |
| 5,202,328 A | 4/1993 | de Laszlo et al. | |
| 5,294,612 A | 3/1994 | Bacon et al. | |
| 5,393,755 A | 2/1995 | Neustadt et al. | |
| 5,824,683 A | 10/1998 | McKittrick et al. | |
| 5,849,770 A | 12/1998 | Head et al. | |
| 5,939,419 A | 8/1999 | Tulshian et al. | |
| 5,962,492 A | 10/1999 | Warrellow et al. | |
| 6,013,621 A | 1/2000 | Nishi et al. | |
| 6,133,273 A | 10/2000 | Gilbert et al. | |
| 6,235,742 B1 | 5/2001 | Bell et al. | |
| 6,235,746 B1 | 5/2001 | Davis et al. | |
| 6,251,904 B1 * | 6/2001 | Bunnage et al. | ......... 514/252.02 |
| 6,316,444 B1 | 11/2001 | Hunt et al. | |
| 6,423,716 B1 | 7/2002 | Matsuno et al. | |
| 6,492,371 B2 | 12/2002 | Roylance | |
| 6,498,165 B1 | 12/2002 | Armstrong et al. | |
| 6,552,029 B1 | 4/2003 | Davis et al. | |
| 6,586,423 B2 | 7/2003 | Bilodeau et al. | |
| 6,599,908 B1 | 7/2003 | Davis et al. | |
| 6,649,608 B2 | 11/2003 | Pease et al. | |
| 6,670,368 B1 | 12/2003 | Breault et al. | |
| 6,693,099 B2 | 2/2004 | Degenhardt et al. | |
| 6,756,373 B1 | 6/2004 | Allerton et al. | |
| 6,969,719 B2 | 11/2005 | Asberom et al. | |
| 7,153,824 B2 | 12/2006 | Palmer et al. | |
| 7,157,451 B2 | 1/2007 | Atwal et al. | |
| 8,273,750 B2 | 9/2012 | Li et al. | |
| 8,273,751 B2 | 9/2012 | Li et al. | |
| 8,536,159 B2 | 9/2013 | Li et al. | |
| 8,633,180 B2 | 1/2014 | Li et al. | |
| 8,664,207 B2 | 3/2014 | Li et al. | |
| 8,697,710 B2 | 4/2014 | Li et al. | |
| 2003/0069246 A1 | 4/2003 | Darrow et al. | |

(Continued)

FOREIGN PATENT DOCUMENTS

| | | |
|---|---|---|
| DE | 19931206 A1 | 1/2001 |
| EP | 0 063 381 A1 | 10/1982 |
| EP | 0 095 289 A2 | 11/1983 |
| EP | 0201188 | 12/1986 |
| EP | 0201188 A2 | 12/1986 |
| EP | 0 636 626 A1 | 2/1995 |
| EP | 0 911 333 A1 | 4/1999 |
| JP | 53031694 A | 3/1978 |
| KR | 10-1991-0006866 | 9/1991 |
| WO | WO 91/19717 | 12/1991 |

(Continued)

OTHER PUBLICATIONS

Pender et al. "Prevention of Autoimmune Attack and Disease Progressionin Multiple Sclerosis: Current Theripies and Future Prospects" Internal Medicine Journal, 2002, vol. 32, No. 11, pp. 554-563.*

(Continued)

*Primary Examiner* — Kendra D Carter
(74) *Attorney, Agent, or Firm* — Hoxie & Associates, LLC

(57) ABSTRACT

The present invention relates to a new use for compounds that inhibit phosphodiesterase 1 (PDE1), e.g., that inhibit PDE1-mediated suppression of the dopamine D1 receptor and/or progesterone signaling pathways, including, e.g., methods of treatment or prophylaxis for conditions which may be ameliorated by enhancing the progesterone signaling response, particularly female sexual dysfunction.

15 Claims, No Drawings

(56) References Cited

U.S. PATENT DOCUMENTS

| | | |
|---|---|---|
| 2003/0092908 A1 | 5/2003 | Pitts et al. |
| 2003/0162782 A1 | 8/2003 | Grossman et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |
| 2006/0229288 A1 | 10/2006 | Palmer et al. |
| 2006/0252790 A1 | 11/2006 | Allen et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2008/0213889 A1 | 9/2008 | Palmer et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li et al. |
| 2013/0018063 A1 | 1/2013 | Li et al. |
| 2013/0085123 A1 | 4/2013 | Li et al. |
| 2013/0239234 A1 | 9/2013 | Greengard et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |

FOREIGN PATENT DOCUMENTS

| | | |
|---|---|---|
| WO | WO 91/19717 A1 | 12/1991 |
| WO | WO 94/19351 A1 | 9/1994 |
| WO | WO 98/46606 A1 | 10/1998 |
| WO | WO 98/52568 A1 | 11/1998 |
| WO | WO 01/27113 A2 | 4/2001 |
| WO | WO 02/074312 A1 | 9/2002 |
| WO | WO 03/002567 A1 | 1/2003 |
| WO | WO 03/020702 A2 | 3/2003 |
| WO | WO 03/020724 A1 | 3/2003 |
| WO | WO 03/042216 A1 | 5/2003 |
| WO | WO 2006/133261 A2 | 12/2006 |
| WO | WO 2006133261 A2 * | 12/2006 |
| WO | WO 2007/143568 A1 | 12/2007 |
| WO | WO 2007143705 | 12/2007 |
| WO | WO 2008/063505 A1 | 5/2008 |
| WO | WO 2009/073210 A1 | 6/2009 |
| WO | WO 2009/075784 A1 | 6/2009 |
| WO | WO 2011/043816 A1 | 4/2011 |
| WO | WO 2011/153129 A1 | 12/2011 |
| WO | WO 2011/153135 A1 | 12/2011 |
| WO | WO 2011/153136 A1 | 12/2011 |
| WO | WO 2011/153138 A1 | 12/2011 |
| WO | WO 2012/171016 A1 | 12/2012 |
| WO | WO 2013/192556 A2 | 12/2013 |

OTHER PUBLICATIONS

Rosenshein, B. "Prevention Menopause" Townsend Letter The Examiner of Alternatiive Medicine, Oct. 2007, pp. 1-7.*
Kraft et al. "Comparison of PDE expression profiles of human prostate and prostate cancer cell lines and the effect of PDE inhibitors on cell proliferation" The FASEB Jornal, 2006, vol. 20, A1131.*
Phillips, N. "Female Sexual Dysfunction: Evaluation and Treatment" Am Fam Physician, Jul. 2000, vol. 62, No. 1, pp. 127-136 (printed pp. 1-14).*
Xia et al. "Synthesis and Evaluation of Polycyclic Pyrazolo[3,4-d]pyrimidines as PdE1 and PDE5 cGMP Phosphodiesterase Inhibitors" J. Med. Chem, 1997, vol. 40, pp. 4372-4377.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Allende, C., et al., "Characterization of Cyclic Nucleotide Phosphodiesterases in Xenopus Laeis Ovary", Comparative Biochemistry and Physiology, vol. 88, No. 2, pp. 581-587, Jan. 1, 1987.
Jiang, M., et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol", Journal of Organic Chemistry, vol. 70, No. 7, pp. 2824-2827, 2005.
Ueckert, S., et al., "Detection of Phosphodiesterase (PDE) Isoenzymes 1,2,10 and 11 in the Human Clitoris by Means of Molecular Biology and Immunohistochemistry", Journal of Urology, vol. 171, No. 4, Suppl., p. 428, Apr. 1, 2004.
Yan, X., et al., "Synthesis and Evaluation of Polycyclic Pyrazoloa 3, 4-Dupryimidines and PDE1 and PDE5 CGMP Phosphodiesterase Inhibitors", Journal of Medicinal Chemistry, vol. 40, No. 26, pp. 4372-4377, Jan. 1, 1997.
Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chem. (1997) 40(14):2196-2210.
Harris, "Pfizer Gives Up Testing Viagra on Women", *The New York Times*, pp. 1-3, (2004).
Al-Afaleq, E. et al., "Heterocyclic o-Aminonitriles: Preparation of Pyrazolo[3,4-d]-pyrimidines with Modification of the Substituents at the 1-Position," Molecules, 2001, 6, 621-638.
"Anxiety," [retrieved on May 14, 2008]. Retrieved online via Internet, URL: http://www.nlm.nih.gov/medlineplus/anxiety.html, 5 pages.
Aswar, M. et al., "Anti-Cataleptic Activity of Various Extracts of *Ocimum sanctum*," International Journal of Pharmaceutical Research and Development, 2010, 2 (6), 7 pages.
"Autism," [retrieved on May 14, 2008]. Retrieved online via Internet, URL: http://www.nlm.nih.gov/medlineplus/autism.html, 6 pages.
Banker, Gilbert S. et al., Eds., Modern Pharmaceutics, Third Edition, Marcel Dekker Inc., New York, 1996.
Bastia, E. et al., "Effect of $A_1$ and $A_{2A}$ Adenosine Receptor Ligands in Mouse Acute Models of Pain," Neuroscience Letters, 2002, 328, 241-244.
Bender, A. et al., "Cyclic Nucleotide Phosphodiesterases: Molecular Regulation to Clinical Use," Pharmacological Reviews, 2006, 58 (3), 488-520.
Blokland, A. et al., "PDE Inhibition and Cognition Enhancement," 2012, 22 (4), 349-354 (abstract only).
Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.
Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-*hi*]indoles: Discovery of Potent, Selective Phosphodiesterase Type 4 Inhibitors," Journal of Medicinal Chemistry, 2000, 43 (25), 4850-4867.
Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.
Chebib, M. et al., "1-Phenylpyrazolo[3,4-*d*]pyrimidines; Structure-Activity Relationships for C6 Substituents at $A_1$ and $A_{2A}$ Adenosine Receptors," Bioorganic & Medicinal Chemistry, 2000, 8, 2581-2590.
Chen, M. et al., "Effects of Bimatoprost 0.03% on Ocular Hemodynamics in Normal Tension Glaucoma," Journal of Ocular Pharmacology and Therapeutics, 2006, 22 (3), 188-193.
Chermat, R. et al., "Adaptation of the Tail Suspension Test to the Rat," Journal de Pharmacologic (Paris), 1986, 17 (3), 348-350.

(56) References Cited

OTHER PUBLICATIONS

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.
Dewald, H. et al., "Synthesis and Potential Antipsychotic Activity of 1H-Imidazo[1,2-c]pyrazolo[3,4-e]pyrimidines," Journal of Medicinal Chemistry, 1988, 31, 454-461.
Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.
Ennaceur, A. et al., "A New One-Trial Test for Neurobiological Studies of Memory in Rats. 1:Behavioral Data," Behavioural Brain Research, 1998, 31, 47-59.
Fienberg, A. et al., "DARPP-32: Regulator of the Efficacy of Dopaminergic Neurotransmission," Science, 1998, 281, 838-842.
Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.
Gelbin, M. et al., "Ketene-S,N-acetals as Synthons for Heterocycles, New Synthesis of Pyrimidinones," Journal Für Praktische Chemie, 1987, 329 (5), 753-766.
Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.
Greengard, P. et al., "Beyond the Dopamine Receptor: The DARPP-32/Protein Phosphatase-1 Cascade," Neuron, 1999, 23, 435-447.
Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.
Hulley, P. et al., "Cyclic AMP Promotes the Survival of Dopaminergic Neurons in vitro and Protects Them from the Toxic Effects of MPP+," Journal of Neural Transmission [Supplementa], 1995, 46, 217-228.
Japanese Patent Office, Patent Abstracts of Japan, Abstract for JP 53031694 A, Date of publication of application Mar. 25, 1978, 1 page.
Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi:10.1186/1471-2202-13-132, 15 pages.
Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Lundqvist, T. et al., "Exploitation of Structural and Regulatory Diversity in Glutamate Racemases," Nature, 2007, 447, 817-822.
Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Murray, F. et al., "Expression and Activity of cAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, 2007, 292, L294-L303.
Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Park, E, et al., "Traumatic Brain Injury: Can the Consequences Be Stopped?" CMAJ, 2008, 178 (9), 1163-1170.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brain*," Acta Physiologica Scandinavica, Supplementum 367, 1971, 1-48.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.

(56) References Cited

OTHER PUBLICATIONS

Wolff, M. Ed., Burger's Medicinal Chemistry and Drug Discovery, Fifth Edition, vol. I: Principles and Practice, John Wiley & Sons, New York, 1995, 975-977.

Xia, Y. et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.

Applicant-Initiated Interview Summary mailed Sep. 13, 2012, Response to 312 Communication mailed Aug. 24, 2012, Applicant-Initiated Interview Summary mailed Jul. 23, 2012, Examiner-Initiated Interview Summary mailed Apr. 18, 2012, Applicant-Initiated Interview Summary mailed Apr. 18, 2012, Notice of Allowance and Fee(s) Due mailed Apr. 18, 2012, Final Office Action mailed Jan. 31, 2012, Non-Final Office Action mailed Aug. 16, 2011, Advisory Action mailed Mar. 30, 2010, Final Office Action mailed Dec. 30, 2009, Non-Final Office Action mailed Aug. 18, 2009, in U.S. Appl. No. 11/916,761, 74 pages.

Requirement for Restriction/Election mailed May 28, 2009, in U.S. Appl. No. 11/916,761, 9 pages.

Final Office Action mailed Apr. 23, 2014, Non-Final Office Action mailed Nov. 4, 2013, in U.S. Appl. No. 13/552,381, 14 pages.

Applicant-Initiated Interview Summary mailed Apr. 26, 2012, Notice of Allowance and Fee(s) Due mailed Apr. 26, 2012, Final Office Action mailed Mar. 27, 2012, Non-Final Office Action mailed Nov. 29, 2011, in U.S. Appl. No. 12/746,236, 27 pages.

Advisory Action mailed Jan. 14, 2014, Final Office Action mailed Oct. 24, 2013, and Non-Final Office Action mailed Apr. 30, 2013, for U.S. Appl. No. 13/486,264, 29 pages.

Notice of Allowance and Fee(s) Due mailed Apr. 25, 2014, Applicant-Initiated Interview Summary mailed Jan. 27, 2014, for U.S. Appl. No. 13/486,264, 12 pages.

\* cited by examiner

METHOD OF TREATING FEMALE SEXUAL DYSFUNCTION WITH A PDE1 INHIBITOR

CROSS REFERENCE TO RELATED APPLICATIONS

This application is a U.S. filing under 35 U.S.C. 371 of PCT/US2007/024866 filed on Dec. 5, 2007, which claims the benefit of U.S. Provisional Application No. 60/873,104 filed on Dec. 5, 2006, the contents of each of which are herein incorporated by reference in their entirety.

TECHNICAL FIELD

The present invention relates to a new use for compounds that inhibit phosphodiesterase 1 (PDE1), e.g., that inhibit PDE1-mediated suppression of the dopamine D1 receptor intracellular pathway and/or the progesterone signaling pathway, e.g., in a method for treating conditions that may be ameliorated through enhanced progesterone signaling, particularly female sexual dysfunction.

BACKGROUND OF THE INVENTION

In the past decade, the success of sildenafil citrate (Viagra®, Pfizer) in the treatment of erectile dysfunction has drawn much attention to the development of sexual dysfunction drugs. The focus, however, has primarily been in treating male sexual dysfunction through the use of phosphodiesterase (PDE) V inhibitors to facilitate smooth muscle relaxation and increase blood flow in the corpus cavernosum.

Eleven families of phosphodiesterases (PDEs) have been identified but only PDEs in Family I, the $Ca^{2+}$-calmodulin-dependent phosphodiesterases (CaM-PDEs), have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases downregulate intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 inhibits the activity of protein phosphatase-1 (PP-1), which helps maintain the state of phosphorylation of many PP-1 substrate proteins, e.g., progesterone receptor (PR), leading to the induction of physiological responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, progesterone receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B may potentiate the effect of a dopamine D1 agonist by protecting cGMP and cAMP from degradation, and similarly inhibit dopamine D2 receptor signaling pathways, by inhibiting PDE1 activity. PDE1 inhibitors are therefore potentially useful in diseases characterized by reduced dopamine D1 receptor signaling activity. See generally, WO 03/020702.

EP 0201188 and EP 0911333, the contents of which are incorporated herein by reference, disclose certain 1,3,5,-substituted, 6,7-dihydro-1H-pyrazolo[4,3-d]pyrimidin-7-one compounds, claimed to be useful for treatment of cardiovascular disease, erectile dysfunction, and other disorders. Although erectile and female sexual dysfunction are disclosed, these compounds are not, however, taught or suggested to be useful for the treatment of diseases involving disorders of the dopamine D1 receptor intracellular pathway, particularly diseases relating to progesterone signaling pathway. PCT/US2006/33179, the contents of which are incorporated herein by reference, discloses the use of 1,3,5,-substituted, 6,7-dihydro-1H-pyrazolo[4,3-d]pyrimidin-7-one compounds for treatment of diseases involving disorders of the dopamine D1 receptor intracellular pathway, but does not specifically disclose the use of such compounds in the enhancement of progesterone signaling pathway associated with female sexual dysfunction. PCT/US2006/022066, the contents of which are incorporated herein by reference, discloses PDE1 inhibitors which are 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, but does not specifically disclose their use for the enhancement of progesterone signaling. WO 03/042216, U.S. Pat. No. 5,939,419, EP 0 538 332, U.S. Pat. No. 5,393,755, U.S. Pat. No. 6,969,719 B2, Xia et al., *J. Med.*

Chem. (1997), 40, 4372-4377 and Ahn et al., *J. Med. Chem.* (1997), 40, 2196-2210, the contents of which are incorporated herein by reference, disclose PDE1/PDE5 cGMP phosphodiesterase inhibitors which are substituted pyrazolo[3,4-d]pyrimidine or imidazo[2,1-b]purin-4-one analogues useful for the treatment of hypertensive, cardiovascular, sexual dysfunction and other cGMP-PDEV related disorders, but do not specifically disclose their use for the enhancement of progesterone signaling, particularly in female sexual dysfunction.

SUMMARY OF THE INVENTION

The invention provides a new method of treatment or prophylaxis of conditions that may be ameliorated by enhancement of progesterone signaling pathways, for example female sexual dysfunction, comprising administering an effective amount of a phosphodiesterase-1 (PDE1) inhibitor to a patient in need thereof. PDE1 inhibitors include, for example, 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form (hereinafter a PDE 1 Inhibitor, e.g., as described below) or a 1,3,5-substituted 6,7-dihydro-1H-pyrazolo[4,3-d]pyrimidin-7-one, in free, salt or prodrug form (also included in PDE 1 Inhibitors, e.g., as described below), to a patient in need thereof.

PDE1 inhibitors also include, for example, substituted imidazo[2,1-b]purin-4-one, e.g., (6aR,9aS)-2-(biphenyl-4-ylmethyl)-5,6a,7,8,9,9a-hexahydro-5-methyl-3(phenylmethyl)-cyclopent-[4,5]imidazo-[2,1-b]purin-4(3H)-one, (6aR,9aS)-5,6a,7,8,9,9a-hexahydro-5-methyl-2,3-bis(phenylmethyl)cyclopent-[4,5]imidazo-[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one, or 5'-methyl-2'-(biphenyl-4-ylmethyl)-3'-(phenylmethyl)spiro[cyclopentane-1,7'(8'H)-[3H]imidazo[2,1-b]purin]-4'(5'H)-one (hereinafter a PDE 1 Inhibitor, e.g., as described below). These compounds are found to selectively inhibit phosphodiesterase 1 (PDE1) activity, especially PDE1B activity, and to be useful for the treatment or prophylaxis of conditions that may be ameliorated by enhancement of progesterone signaling pathways such as female sexual dysfunction.

DETAILED DESCRIPTION OF THE INVENTION

Compounds for Use in the Methods of the Invention

Preferably, the PDE 1 Inhibitors for use in the methods of treatment described herein are a 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, of formula I:

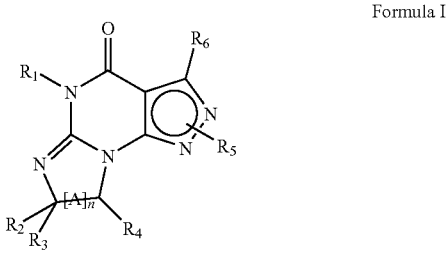

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl or
$R_5$ is attached to one of the nitrogens on the pyrazolo portion of Formula I and is a moiety of Formula Q

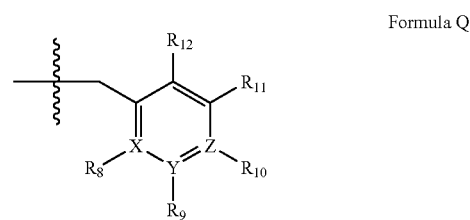

Formula Q wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), hetarylamino, N,N-dialkylamino, N,N-diarylamino, or N-aryl-N-(arylakyl)amino (e.g., N-phenyl-N-(1,1'-biphen-4-ylmethyl)amino); and
(v) n=0 or 1;
(vi) when n=1, A is —$C(R_{13}R_{14})$—
wherein $R_{13}$ and $R_{14}$, are, independently, H or $C_{1-4}$ alkyl, aryl, heteroaryl, (optionally hetero)arylalkoxy or (optionally hetero)arylalkyl;
in free, salt or prodrug form, including its enantiomers, diasterisomers and racemates.

The invention further provides the use of PDE 1 Inhibitors of Formula I as follows:
1.1 Formula I wherein $R_1$ is methyl and n=0;
1.2 Formula I or 1.1 wherein $R_4$ is H or $C_{1-4}$ alkyl and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
1.3 Formula I or 1.1 wherein $R_4$ is H and at least one of $R_2$ and $R_3$ is arylalkoxy;
1.4 Formula I wherein $R_1$ is methyl, $R_2$, $R_3$, and $R_4$ are H, n=1, and $R_{13}$ and $R_{14}$ are, independently, H or $C_{1-4}$ alkyl (e.g., methyl or isopropyl);
1.5 Formula I or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;
1.6 Formula I, 1.1 or 1.5 wherein $R_5$ is a substituted heteroarylmethyl, e.g., para-substituted with haloalkyl;
1.7 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is phenyl;
1.8 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is pyridyl or thiadiazolyl;

1.9 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H or halogen, and $R_{10}$ is haloalkyl;

1.10 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H, and $R_{10}$ is alkyl sulfonyl;

1.11 any of the preceding formulae wherein $R_5$ is attached to the 2-position nitrogen on the pyrazolo ring;

1.12 any of the preceding formulae wherein $R_6$ is benzyl;

1.13 any of the preceding formulae wherein $R_6$ is phenylamino or phenylalkylamino (e.g., benzylamino);

1.14 any of the preceding formulae wherein $R_6$ is phenylamino;

1.15 any of the preceding formulae wherein X, Y, and Z are all C, 1.16 any of the preceding formulae wherein X, Y, and Z are all C and $R_{10}$ is phenyl or 2-pyridyl; and/or 1.17 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 µM, preferably less than 25 nM in an immobilized-metal affinity particle reagent PDE assay, for example, as described in Example 1;

in free or salt form.

For example, the PDE 1 Inhibitors include 7,8-dihydro-[1H or 2H]-imidazo[1,2-a]pyrazolo[4,3-e]pyrimidin-4(5H)-ones of Formula Ia

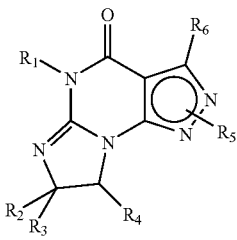

Formula Ia wherein
(i) $R_1$ is H or $C_{1-4}$ alkyl [e.g., methyl];
(ii) $R_4$ is H and $R_2$ and $R_3$ are, independently, H or $C_{1-4}$ alkyl [e.g., $R_2$ and $R_3$ are both methyl, or $R_2$ is H and $R_3$ is isopropyl], aryl, or arylalkyl;
or $R_2$ is H and $R_3$ and $R_4$ together form a di-, tri- or tetramethylene bridge [pref. wherein the $R_3$ and $R_4$ have the cis configuration, e.g., where the carbons carrying $R_3$ and $R_4$ have the R and S configurations respectively];
(iii) $R_5$ is attached to one of the nitrogens on the pyrazolo portion of formula Ia and is a substituted benzyl of formula B

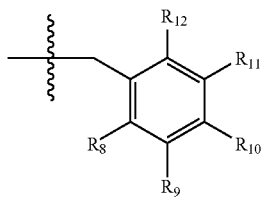

Formula B wherein $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), arylcarbonyl (e.g., benzoyl), alkyl sulfonyl or heteroarylcarbonyl; and (iv) $R_6$ is H, alkyl, aryl, heteroaryl, arylalkyl [e.g., benzyl], arylamino [e.g., phenylamino], heteroarylamino, arylalkylamino, N,N-dialkylamino, N,N-diarylamino, or N-aryl-N-(arylalkyl)amino [e.g. N-phenyl-N-(1,1'-biphen-4-ylmethyl)amino];

in free, salt or prodrug form.

The invention further provides the use of PDE 1 Inhibitors of Formula Ia as follows:

2.1: Formula Ia wherein $R_1$ is methyl;

2.2: Formula Ia or 2.1 wherein $R_4$ is H and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;

2.3: Formula Ia or 2.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;

2.4: Formula Ia, 2.1, 2.2 or 2.3 wherein $R_5$ is a moiety of formula B wherein $R_8$, $R_9$, $R_{11}$, and $R_{12}$ are H and $R_{10}$ is phenyl;

2.5: Formula Ia, 2.1, 2.2, or 2.3 wherein $R_5$ is a moiety of formula B wherein $R_8$, $R_9$, $R_{11}$, and $R_{12}$ are H and $R_{10}$ is pyridyl or thiadiazolyl;

2.6: Formula Ia, 2.1, 2.2, 2.3, 2.4, or 2.5 wherein $R_5$ is attached to the 2-position nitrogen on the pyrazolo ring;

2.7: Formula Ia, 2.1, 2.2, 2.3, 2.4, 2.5 or 2.6 wherein $R_6$ is benzyl;

2.8: Formula Ia, 2.1, 2.2, 2.3, 2.4, 2.5 or 2.6 wherein $R_6$ is phenylamino or phenylalkylamino (e.g., benzylamino); and/or 2.9: Formula Ia, 2.1, 2.2, 2.3, 2.4, 2.5, 2.6, 2.7, or 2.8 wherein the compounds inhibit phosphodiesterase-mediated (e.g., PDE1-mediated, especially PDE1B-mediated) hydrolysis of cGMP, e.g., with an $IC_{50}$ of less than 1 µM, preferably less than 25 nM in an immobilized-metal affinity particle reagent PDE assay, for example, as described in Example 1; in free or salt form.

In an another embodiment, the PDE 1 Inhibitors are compounds of Formula I wherein
(i) $R_1$ is methyl;
(ii) $R_2$, $R_3$ and $R_4$ are H;
(iii) n=1 and $R_a$ and $R_b$, are, independently, H or methyl;
(iv) $R_5$ is a moiety of Formula Q wherein $R_8$, $R_9$, $R_{11}$ and $R_{12}$ are H and $R_{10}$ is phenyl, pyridyl (for example pyrid-2-yl), or thiadiazolyl (e.g., 1,2,3-thiadiazol-4-yl);
(v) $R_6$ is benzyl, phenylamino or benzylamino;
in free or salt form.

In another embodiment, the PDE 1 Inhibitors are compounds of Formula I wherein
(i) $R_1$ is methyl;
(ii) n=0;
(iii) $R_2$ is H and $R_3$ and $R_4$ together form a tri- or tetramethylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
(iv) $R_5$ is a substituted heteroarylmethyl, e.g., para-substituted with haloalkyl; or
$R_5$ is a moiety of Formula Q wherein $R_8$, $R_9$, $R_{11}$ and $R_{12}$ are H or halogen and $R_{10}$ is haloalkyl, phenyl, pyridyl (for example pyrid-2-yl), or thiadiazolyl (e.g., 1,2,3-thiadiazol-4-yl); and (v) $R_6$ is benzyl, phenylamino or benzylamino; in free or salt form.

In another embodiment, the PDE 1 Inhibitors are compounds of Formula Ia wherein
(i) $R_1$ is methyl;
(ii) $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
(iii) $R_5$ is a moiety of Formula B wherein $R_8$, $R_9$, $R_{11}$, and $R_{12}$ are H and $R_{10}$ is haloalkyl, phenyl, pyridyl (for example pyrid-2-yl), or thiadiazolyl (e.g., 1,2,3-thiadiazol-4-yl); and
(iv) $R_6$ is benzyl, phenylamino or benzylamino; in free or salt form.

In another embodiment, the PDE 1 Inhibitors are compounds of Formula Ia selected from the following:

Compound 1

Compound 2

For example, PDE 1 Inhibitors include compounds according to Formulae II, III and IV.

Formula II wherein
$R_a$ and $R_b$ are, independently, H or $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

Formula III wherein
$R_2$ is H and $R_3$ and $R_4$ together form a tri- or tetra-methylene bridge [pref. with the carbons carrying $R_3$ and $R_4$ having the R and S configuration respectively];
or at least one of $R_2$ and $R_3$ is methyl, isopropyl or arylalkoxy and $R_4$ is H; or
$R_2$ and $R_3$ are H and $R_4$ is a $C_{1-4}$ alkyl;
$R_6$ is phenylamino or benzylamino;
$R_{10}$ is haloalkyl, phenyl, pyridyl (for example pyrid-2-yl), or thiadiazolyl (e.g., 1,2,3-thiadiazol-4-yl);
in free or salt form.

Formula IV wherein
$R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

In a preferred embodiment, the PDE 1 Inhibitors for use in the methods of treatment described herein are a 1,3,5-substituted 6,7-dihydro-1H-pyrazolo[4,3-d]pyrimidin-7-one, of formula V (V)

wherein
$R_a$ is methyl or $C_2$-$C_6$ alkyl;
$R_1$ is H or $C_1$-$C_4$ alkyl;

each of $R_2$ and $R_3$ is independently selected from H and $C_1$-$C_4$ alkyl, or $R_2$ is H or $C_1$-$C_4$ alkyl and $R_3$ is OH, $C_2$-$C_4$ alkanoyloxy or fluoro, or $R_2$ and $R_3$ when taken together represent $C_2$-$C_6$ alkylene, or $R_2$ and $R_3$ when taken together with the carbon atom to which they are attached represent a carbonyl group;

Ar is either (a)

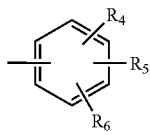

Wherein
each of $R_4$, $R_5$ and $R_6$ is independently selected from
H
$C_1$-$C_4$ alkyl,
$C_1$-$C_4$ alkoxy,
$C_1$-$C_4$ alkoxy-Z—,
halo,
halo($C_1$-$C_4$)alkyl,
phenoxy, optionally substituted by up to three substitutents each of which substituent is independently selected from halo, $C_{1-4}$ alkyl, and $C_1$-$C_4$ alkoxy,
nitro,
hydroxy,
hydroxy-Z—,
$C_2$-$C_4$ alkanoyl,
amino,
amino-Z—,
($C_1$-$C_4$ alkyl)NH,
($C_1$-$C_4$ alkyl)$_2$N—,
($C_1$-$C_4$ alkyl)NH—Z—,
($C_1$-$C_4$ alkyl)$_2$N—Z—,
—COOH,
—Z—COOH,
—COO($C_1$-$C_4$ alkyl),
—Z—COO($C_1$-$C_4$ alkyl)
$C_1$-$C_4$ alkanesulphonamido,
$C_1$-$C_4$ alkanesulphonamido-Z—,
halo($C_1$-$C_4$)alkanesulphonamido,
halo($C_1$-$C_4$)alkanesulphonamido-Z—,
$C_1$-$C_4$ alkanamido,
$C_1$-$C_4$ alkanamido-Z—,
HOOC—Z—NH—,
HOOC—Z—NH—Z—,
($C_1$-$C_4$ alkyl)OOC—Z—NH—,
($C_1$-$C_4$ alkyl)C—Z—NH—Z—,
$C_1$-$C_4$ alkyl-NH—SO$_2$—NH—,
$C_1$-$C_4$ alkyl-NH—SO$_2$—NH—Z—,
($C_1$-$C_4$ alkyl)$_2$-N—SO$_2$—NH—,
($C_1$-$C_4$ alkyl)$_2$-N—SO$_2$—NH—Z—,
$C_1$-$C_4$ alkoxy CH=CH—Z—CONH—,
$C_1$-$C_4$ alkoxy CH=CHCONH
$C_1$-$C_4$ alkyl-SO$_2$—N($C_1$-$C_4$ alkyl)-,
$C_1$-$C_4$ alkyl-SO$_2$—N($C_1$-$C_4$ alkyl)-Z—,
($C_1$-$C_4$ alkyl)NH—Z—SO$_2$—NH—,
($C_1$-$C_4$ alkyl)$_2$N—Z—SO$_2$—NH—,
($C_1$-$C_4$ alkyl)NH—Z—SO$_2$—NH—Z—,
($C_1$-$C_4$ alkyl)$_2$N—Z—SO$_2$—NH—Z—,
benzenesulphonamido, optionally ring substituted by up to three substituents each of which is independently selected from halo, $C_{1-4}$ alkyl, and $C_1$-$C_4$ alkoxy,
$C_1$-$C_4$ alkanoyl-N($C_1$-$C_4$ alkyl)-,
$C_1$-$C_4$ alkanoyl-N($C_1$-$C_4$ alkyl)-Z—,
$C_1$-$C_4$ alkoxycarbonyl-CH(CH$_2$OH)NHSO$_2$—,
—SO$_3$H,
—SO$_2$NH$_2$,
H$_2$NOC—CH(CH$_2$OH)—NHSO$_2$—,
HOOC—Z—O—, and
($C_1$-$C_4$ alkyl)OOC—Z—O—,
or optionally one of $R_4$, $R_5$ and $R_6$ is a G-Het group and wherein the others of $R_4$, $R_5$ and $R_6$ are independently selected from the $R_4$, $R_5$ and $R_6$ substitutents listed above;

Z is $C_1$-$C_4$ alkylene,
G is a direct link, Z, O, —SO$_2$NH—, SO$_2$, or —Z—N($C_1$-$C_4$ alkyl)SO$_2$—,
Het is a 5- or 6-membered heterocyclic group containing 1, 2, 3 or 4 nitrogen heteroatoms; or 1 or 2 nitrogen heteroatoms and 1 sulphur heteroatom or 1 oxygen heteroatom; or the heterocyclic group is furanyl or thiophenyl; wherein the Het group is saturated or partially or fully unsaturated and optionally substituted by up to 3 substituents, wherein each substitutent is independently selected from $C_1$-$C_4$ alkyl, oxo, hydroxy, halo, and halo($C_1$-$C_4$) alkyl;

or (b) any one of the following bicyclic groups:
benzodioxolanyl,
benzodioxanyl,
benzimidazolyl,
quinolinyl,
indolyl,
quinazolinyl,
isoquinolinyl,
benzotriazolyl,
benzofuranyl,
benzothiophenyl,
quinoxalinyl, or
phthalizinyl,
wherein said bicyclic Ar groups are linked to the neighbouring —C($R_2R_3$)— group via the benzo ring portion,
and wherein the heterocyclic portion of said bicyclic Ar group is optionally partially or fully saturated, said group being optionally substituted by one or more of $C_1$-$C_4$ alkyl, halo, hydroxy, oxo, amino, and $C_1$-$C_4$ alkoxy;
or a pharmaceutically acceptable salt of the compound, or a pharmaceutically acceptable solvate of the compound or the salt.

For example, PDE 1 Inhibitors for use in the present invention include 1,3,5,-substituted, 6,7-dihydro-1H-pyrazolo[4,3-d]pyrimidin-7-one, in free or pharmaceutically acceptable salt form, particularly compounds of Formula V or the following formulae:

3.2 Of Formula V wherein $R_a$ is a $C_{2-5}$ alkyl group;
3.3 Of Formula V wherein $R_a$ is a $C_{2-4}$ alkyl group.
3.4 Of Formula V wherein $R_a$ is a $C_3$ alkyl group.
3.5 Of Formula V wherein $R_a$ is methyl
3.6 Of Formula V, 3.2, 3.3, 3.4 or 3.5 wherein $R_1$ is a $C_{1-6}$ alkyl group.
3.7 Of any of the preceding formulae wherein $R_1$ is a $C_{1-3}$ alkyl group.
3.8 Of any of the preceding formulae wherein $R_1$ is a methyl group.
3.9 Of any of the preceding formulae wherein $R_2$ is H.
3.10 Of any of the preceding formulae wherein $R_3$ is H.

3.11 Of any of the preceding formulae wherein $R_4$, $R_5$ and $R_6$ are independently selected from $H$, $(C_{1-4}$ alkyl$)_2N$—, $C_{1-4}$ alkanesulphonamido and benzenesulphonamido.

3.12 Of any of the preceding formulae wherein $R_4$, $R_5$ and $R_6$ are independently selected from H, diethylamino, methanesulphonamido and benzenesulphonamido.

3.13 Of any of the preceding formulae wherein Ar is 4-diethylaminophenyl.

3.14 Of any of the preceding formulae wherein Ar is 2-methanesulphonamidophenyl.

3.15 Of any of the preceding formulae wherein Ar is 4-benzenesulphonamidophenyl.

3.16 Of any of the preceding formulae wherein one of $R_4$, $R_5$ and $R_6$ is $(C_{1-4}$ alkyl$)_2N$— and wherein the other two of $R_4$, $R_5$ and $R_6$ are H.

3.17 Of any of the preceding formulae wherein one of $R_4$, $R_5$ and $R_6$ is diethylamino and wherein the other two of $R_4$, $R_5$ and $R_6$ are H.

3.18 Of any of the preceding formulae wherein $R_a$ is methyl.

3.19 Of any of the preceding formulae wherein $R_a$ is $C_2$-$C_6$ alkyl.

3.20 Of any of the preceding formulae wherein the compound is selected from the following:

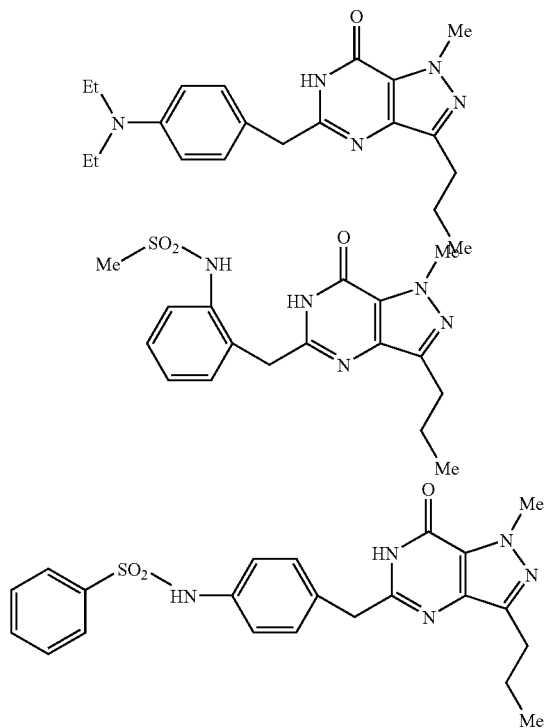

3.21 Of any of the preceding formulae wherein the compound is

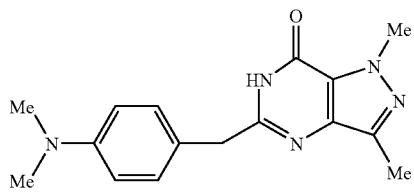 [SMILES: Cc1nn(C)c2c(=O)[nH]c(Cc3ccc(N(C)C)cc3)nc12]

3.22 A compound which is a 1,3,5,-substituted, 6,7-dihydro-1H-pyrazolo[4,3-d]pyrimidin-7-one, in free or pharmaceutically acceptable salt form, e.g. a compound of Formula V or according to any of formulae 3.2-3.21, wherein the compound inhibits phosphodiesterase-mediated (e.g., PDE1-mediated, especially PDE1B-mediated) hydrolysis of cGMP, e.g., with an $IC_{50}$ of less than 1 µM, preferably less than 25 nM in an immobilized-metal affinity particle reagent PDE assay, for example, as described in Example 1 below.

In another embodiment, the PDE 1 Inhibitors for use in the methods of treatment described herein are substituted imidazo[2,1-b]purin-4-one of Formula VIIa or VIIb:

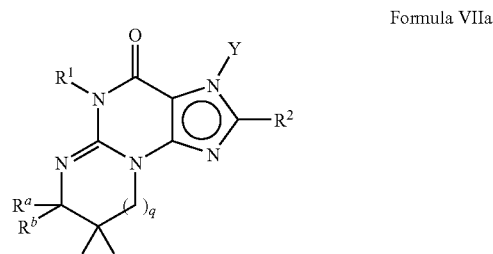

Formula VIIa

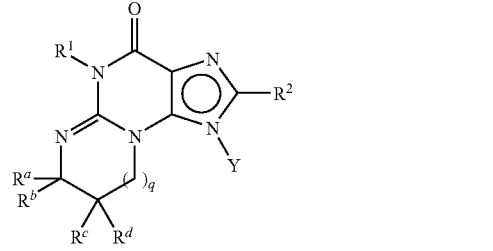

Formula VIIb in free, salt or prodrug form, including its enantiomers, diasterisomers and racemates, wherein:

i) q=0, 1 or 2;

ii) $R^1$, $R^a$, $R^b$, $R^c$ and $R^d$ are each independently H, alkyl, aryl, heteroaryl, cycloalkyl or heterocycloalkyl groups, wherein each alkyl group of $R^1$, $R^a$, $R^b$, $R^c$ and $R^d$ is independently unsubstituted or substituted with 1 to 5 independently selected $R^3$ moieties which can be the same or different, each $R^3$ moiety being independently selected from the group consisting of hydroxy, alkoxy, cycloalkoxy, aryloxy, alkylthio, arylthio, aryl, haloaryl, heteroaryl, cycloalkyl, heterocycloalkyl, amino, alkylamino, dialkylamino, cycloalkylamino and heterocycloalkylamino groups;

wherein each of the aryl, heteroaryl, cycloalkyl and heterocycloalkyl groups of $R^1$, $R^a$, $R^b$, $R^c$ and $R^d$ is independently unsubstituted or substituted with 1 to 5 independently selected $R^4$ moieties which can be the same or different, each $R^4$ moiety being independently selected from the group consisting of: halo, optionally substituted aryl (e.g., phenyl, chlorophenyl, methoxyphenyl), heteroaryl (e.g., pyridyl, pyrrolyl), nitro, cyano, haloalkyl, haloalkoxy, alkyl, alkoxy, cycloalkyl, heterocycloalkyl (e.g., pyrrolidinyl, morpholin-4-yl, pyrrol-1-yl), cycloalkylalkyl, amino, alkylamino, dialkylamino, —$OCF_3$, acyloxy, —$OR^8$, —$C(O)R^9$, —$C(O)OR^8$, —$NR^{10}C(O)R^9$, —$NR^{10}C(O)OR^8$, —$NR^{10}S(O)_2R^9$, —$S(O)_{0-2}R^9$ groups, carbonyl when two hydrogens attached to the same carbon atom of the cycloalkyl or heterocycloalkyl group of R' are substituted, and =$CR^8R^9$ when two hydrogens attached to the same carbon atom of the cycloalkyl or heterocycloalkyl groups of $R^1$ are substituted, wherein each of the aryl, heteroaryl, cycloalkyl and heterocycloalkyl groups of the $R^3$ and $R^4$ moieties above is independently unsubstituted or substituted with 1 to 5 independently selected $R^{12}$ moieties which can be the same or different, each $R^{12}$ moiety being independently selected from the group consisting of: halo, phenyl, nitro, cyano, haloalkyl, haloalkoxy, alkyl, cycloalkyl, cycloalkylalkyl, amino, alkylamino, —$OCF_3$, acyloxy, —$OR^8$, —$C(O)R^9$, —$C(O)OR^8$, —$NR^{10}C(O)R^9$, —$NR^{10}C(O)OR^8$, —$NR^{10}S(O)_2R^9$, —$S(O)_{0-2}R^9$ groups, carbonyl when two hydrogens attached to the same carbon atom of the cycloalkyl or heterocycloalkyl group of $R^3$ or $R^4$ are substituted, and =$CR^8R^9$ when two hydrogens attached to the same carbon atom of the cycloalkyl or heterocycloalkyl group of $R^3$ or $R^4$ are substituted; or iii) $R^a$ and $R^b$, together with the carbon to which they are both attached, form a 4- to 7-membered cycloalkyl or heterocycloalkyl ring, and $R^c$ and $R^d$ are each independently H or an alkyl group; or iv) $R^a$ and $R^c$, together with the respective carbons to which they are attached, form a 4- to 7-membered cycloalkyl or heterocycloalkyl ring, and $R^b$ and $R^d$ are each independently H or an alkyl group, preferably $R^a$ and $R^c$ together have the cis configuration, e.g., where the carbons carrying $R^a$ and $R^c$ have the R and S configurations, respectively;

v) $R^2$ is H, halo, alkyl, haloalkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group,
wherein each alkyl group of $R^2$ is independently unsubstituted or substituted with 1 to 5 independently selected $R^{13}$ moieties which can be the same or different, each $R^{13}$ moiety being independently selected from the group consisting of halo, hydroxy, alkoxy, alkyl, aryl (e.g., phenyl, naphthyl) heteroaryl (e.g., 1H-imidazol-2-yl), cycloalkyl, heterocycloalkyl (e.g., pyrrolidin-1-yl), amino, monoalkylamino or dialkylamino group,
wherein each aryl group of $R^{13}$ is independently unsubstituted or substituted with 1 to 5 independently selected $R^4$ moieties which can be the same or different;

vi) Y is H or an alkyl group substituted with (i) an aryl, heteroaryl, cycloalkyl, hydroxy, alkoxy, amino, monoalkylamino or dialkylamino group, or (ii) an aryl group substituted with from one to three moieties each independently selected from the group consisting of: halo, alkyl, phenyl, hydroxy, alkoxy, phenoxy, amino, monoalkylamino and dialkylamino group;

vii) each $R^8$ is independently H, alkyl or aryl;

viii) each $R^9$ is independently H, alkyl, aryl or —$NR^{10}R^{11}$;

ix) each $R^{10}$ is independently H, alkyl, aryl, heteroaryl, arylalkyl or heteroarylalkyl, wherein each alkyl, aryl, heteroaryl, arylalkyl or heteroarylalkyl of $R^{10}$ is unsubstituted or independently substituted with 1 to 5 $R^{14}$ moieties which can be the same or different, each $R^{14}$ moiety being independently selected from the group consisting of halo, alkyl, aryl, cycloalkyl, —$CF_3$, —$OCF_3$, —CN, —$OR^8$, —$CH_2OR^8$, —$C(O)OR^8$ and —$C(O)NR^8R^8$; and x) each $R^{11}$ is independently H, alkyl, aryl, heteroaryl, arylalkyl or heteroarylalkyl, wherein each alkyl, aryl, heteroaryl, arylalkyl or heteroarylalkyl of $R^{11}$ is unsubstituted or independently substituted with 1 to 5 $R^{14}$ moieties which can be the same or different.

The invention further provides the use of PDE 1 Inhibitors of Formula VIIa or VIIb, in free or salt form, as follows:

4.1: Formula VIIa or VIIb, wherein q=0, 1 or 2;

4.2: Formula VIIa or VIIb, wherein q=0;

4.3: Formula VIIa or VIIb or 4.1 or 4.2, wherein $R^1$ is alkyl;

4.4: Formula VIIa or VIIb or 4.1-4.2, wherein $R^1$ is methyl;

4.5: Formula VIIa or VIIb or 4.1-4.4, wherein $R^a$ and $R^c$, together with the respective carbons to which they are attached, form a 4- to 7-membered cycloalkyl or heterocycloalkyl ring, and $R^b$ and $R^d$ are each independently H or an alkyl group;

4.6: Formula VIIa or VIIb or 4.1-4.4, wherein $R^a$ and $R^c$, together with the respective carbons to which they are attached, form a 5-membered heterocycloalkyl ring, and $R^b$ and $R^d$ are each independently H, 4.7: Formula VIIa or VIIb or 4.1-4.4, wherein $R^a$ and $R^b$, together with the respective carbons to which they are attached, form a 5-membered heterocycloalkyl ring, and $R^c$ and $R^d$ are each independently H, 4.8: Formula VIIa or VIIb or 4.1-4.7, wherein $R^2$ is alkyl or haloalkyl;

4.9: Formula VIIa or VIIb or 4.1-4.7, wherein $R^2$ is biphenyl-4-ylmethyl;

4.10: Formula VIIa or VIIb or 4.1-4.7, wherein $R^2$ is benzyl;

4.11: Formula VIIa or VIIb or 4.1-4.7, wherein $R^2$ is cyclopentylmethyl;

4.12: Formula VIIa or VIIb or 4.1-4.7, wherein $R^2$ is cyclopropylmethyl;

4.13: Formula VIIa or VIIb or 4.1-4.12, wherein Y is benzyl; and/or 4.14: Of any of the preceding formulae wherein the compound is selected from the following:

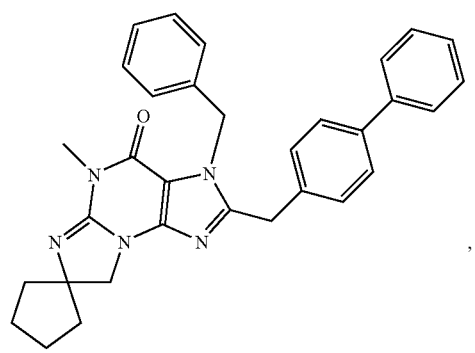

,

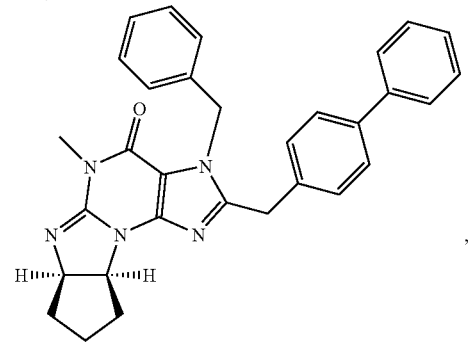

,

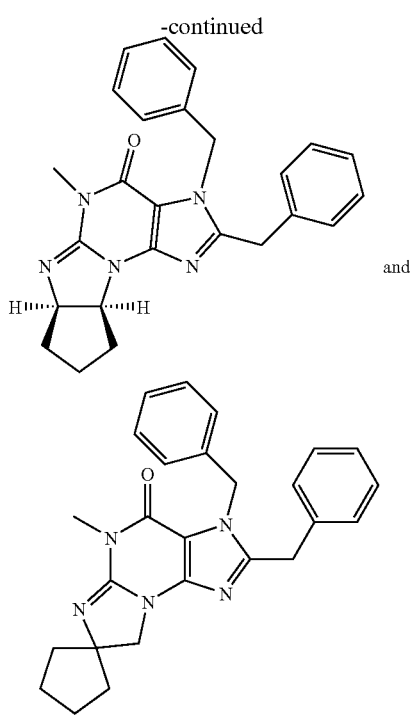

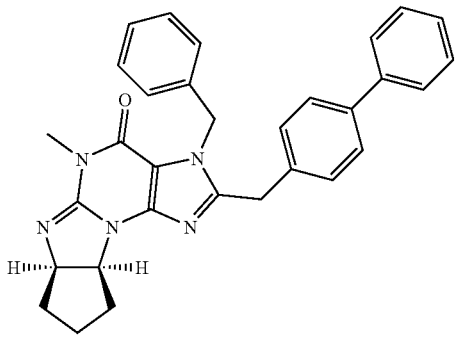 [SMILES: CN1C(=O)c2c(nc(Cc3ccc(-c4ccccc4)cc3)n2Cc2ccccc2)N2C1=N[C@@H]1CCC[C@@H]12]

4.15: Of any of the preceding formulae wherein the compound is

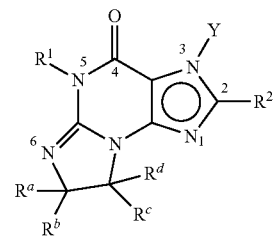

4.16: A compound which is a substituted imidazo[2,1-b]purin-4-one, in free or pharmaceutically acceptable salt form, e.g. a compound of Formula VIIa or according to any of formulae 4.1-4.15, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

Preferably, compounds of Formula VIIa or VIIb are selected from a group consisting of (6aR,9aS)-5,6a,7,8,9,9a-hexahydro-5-methyl-2,3-bis(phenylmethyl)-yclopent[4,5]imidazo[2,1-b]purin-4(3H)-one, (6aR,9aS)-2-(biphenyl-4-ylmethyl)-5,6a,7,8,9,9a-hexahydro-5-methyl-3-(phenylmethyl)cyclopent[4,5]imidazo[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one and 5'-methyl-2'-(biphenyl-4-ylmethyl)-3'-(phenylmethyl)spiro-[cyclopentane-1,7'(8'H)-[3H]imidazo[2,1-b]purin]-4'(5'H)-one, in free or pharmaceutically acceptable salt form.

In an especially preferred embodiment, compound of Formula VIIa is (6aR,9aS)-2-(biphenyl-4-ylmethyl)-5,6a,7,8,9,9a-hexahydro-5-methyl-3-(phenylmethyl)cyclopent-[4,5]imidazo[2,1-b]purin-4(3H)-one, in free or salt form.

The numbering of substituted imidazo[2,1-b]purin-4-one of Formula VIIa or VIIb as described herein is shown below as an example, wherein q=0:

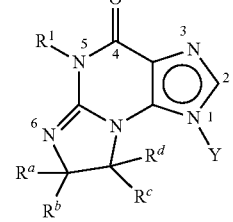

Formula VIIa

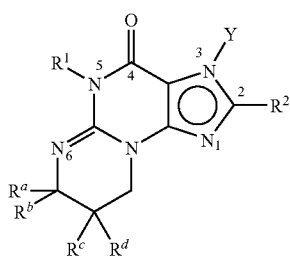

Formula VIIb wherein q=1:

Formula VIIa

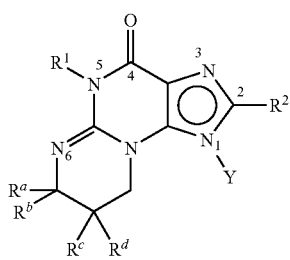

Formula VIIb

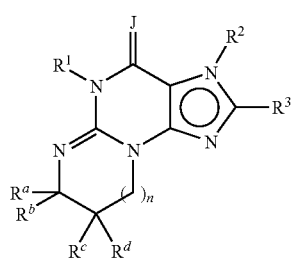

In another embodiment, the PDE 1 Inhibitors for use in the methods of treatment described herein are Compounds of Formula VIIIa or VIIIb:

Formula VIIIa

-continued

Formula VIIIb

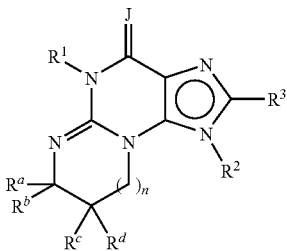

in free or salt form, wherein:
J is oxygen or sulfur,
$R^1$ is hydrogen, alkyl or alkyl substituted with aryl or hydroxy;
$R^2$ is hydrogen, aryl, heteroaryl, cycloalkyl, alkyl or alkyl substituted with aryl, heteroaryl, hydroxy, alkoxy, amino, monoalkyl amino or dialkylamino, or —$(CH_2)_m TCOR^{20}$ wherein m is an integer from 1 to 6, T is oxygen or —NH— and $R^{20}$ is hydrogen, aryl, heteroaryl, alkyl or alkyl substituted with aryl or heteroaryl;
$R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;
$R^a$, $R^b$, $R^c$ and $R^d$ independently represent hydrogen, alkyl, cycloalkyl or aryl; or ($R^a$ and $R^b$) or ($R^c$ and $R^d$) or ($R^b$ and $R^c$) can complete a saturated ring of 5- to 7-carbon atoms, or ($R^a$ and $R^b$) taken together and ($R^b$ and $R^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and
n is zero or one.

The invention further provides the use of PDE 1 Inhibitors of Formula VIIIa or VIIIb, in free or salt form, as follows:
5.1: Formula VIIIa or VIIIb, wherein J=O.
5.2: Formula VIIIa or VIIIb or 5.1, wherein $R^1$ is alkyl.
5.3: Formula VIIIa or VIIIb, 5.1 or 5.2, wherein $R^2$ is hydrogen, benzyl, 4-chlorobenzyl, cyclohexylmethyl or trimethylacetoxymethyl.
5.4: Formula VIIIa or VIIIb, 5.1, 5.2 or 5.3, wherein $R^3$ is hydrogen, or alkyl such as methyl or ethyl.
5.5: Formula VIIIa or VIIIb, 5.1, 5.2, 5.3 or 5.4, wherein n is zero; and
5.6: Formula VIIIa or VIIIb, 5.1, 5.2, 5.3, 5.4 or 5.5, wherein $R^a$ and $R^b$ form a saturated 5 membered ring, or ($R^b$ and $R^c$) form a saturated 5, 6 or 7 membered ring, or ($R^a$ and $R^b$) and ($R^b$ and $R^c$) each complete a saturated ring and each ring contains 5 or 6 carbon atoms.

The invention further provides the use of PDE 1 Inhibitors of Formula VIIIa or VIIIb, in free or salt form, selected from the following:
cis-5,6a,7,8,9,9a-Hexahydro-5-methyl-3-(phenylmethyl)cyclopenta[4,5]imidazo-[2,1-b]purin-4-one;
7,8-Dihydro-5-methyl-3-(phenylmethyl)-3H-imidazo[2,1-b]purin-4(5H)-one;
cis-6a,7,8,9,10,10a-Hexahydro-5-methyl-3-(phenylmethyl)-3H-benzimidazo[2,1-b]purin-4(5H)-one;
5,7,8,9-Tetrahydro-5-methyl-3-(phenylmethyl)pyrimido[2,1-b]purin-4(3H)-one;
7,8-Dihydro-8-phenyl-5-methyl-3-(phenylmethyl)-3H-imidazo[2,1-b]purin-4(5H)-one;
5',7'-Dihydro-5'-methyl-3'-(phenylmethyl)spiro[cyclohexane-1,8'-(8'H)imidazo-[2,1-b]purin]-4'(3'H)-one;
cis-5,6a,11,11a-Tetrahydro-5-methyl-3-(phenylmethyl)indeno[1',2':4,5]imidazo-[2,1-b]purin-4(3H)-one;
5',7'-Dihydro-2',5'dimethyl-3'-(phenylmethyl)spiro{cyclohexane-1,7'(8'H)-imidazo[2,1-b]purin}-4'-(3'H)-one;
7,8-Dihydro-2,5,7,7,8(R,S)-pentamethyl-3H-imidazo[2,1-b]purin-4(5H)-one;
cis-5,6a,7,11b-Tetrahydro-5-methyl-3-(phenylmethyl)indeno[2',1':4,5]imidazo[2,1-b]purin-4(3H)-one;
cis-5,6a,7,8,9,9a-Hexahydro-2,5-dimethyl-3-(phenylmethyl)cyclopent[4,5]-imidazo[2,1-b]purin-4-(3H)-one;
5'-Methyl-3'-(phenylmethyl)-spiro[cyclopentane-1,7'-(8'H)-(3'H)imdazo[2,1-b]purin]-4-(5'H)-one;
7,8-Dihydro-2,5,7,7-tetramethyl-3-(phenylmethyl)-3H-imidazo[2,1-b]purin-4(5'H)-one;
7,8-Dihydro-7(R)-phenyl-2,5-dimethyl-3-(phenylmethyl)-3H-imidazo[2,1-b]purin-4(5H)-one;
7,8-Dihydro-2,5-dimethyl-3,7(R)-bis(phenylmethyl)-3H-imidazo[2,1-b]purin-4(5H)-one;
(±)-7,8-Dihydro-2,5-dimethyl-7-ethyl-3-(phenylmethyl)-3H-imidazo[2,1-b]purin-4(5H)-one;
6a(S)-7,8,9,10,10a(R)-Hexhydro-2,5-dimethyl-3-(phenylmethyl)-3H-benzimidazo[2,1-b]purin-4(5H)-one;
6a(R)-7,8,9,10,10a(S)-hexahydro-2,5-dimethyl-3-(phenylmethyl)-3H-benzimidazo-[2,1-b]purin-4(5H)-one;
7,8-Dihydro-2,5-dimethyl-7(R)-isopropyl-3-(phenylmethyl)-3H-imidazo[2,1-b]purin-4(5H)-one;
7,8-Dihydro-2,5,7(R)-trimethyl-3-(phenylmethyl)-3H-imidazo[2,1-b]purin-4(5H)-one;
cis-7,7a,8,9,10,10a-Hexahydro-2,5-dimethyl-3-(phenylmethyl)-3H-cyclopenta-[5,6]pyrimido[2,1-b]purin-4(5H)-one;
7,8-Dihydro-2,5-dimethyl-7(S)-(1-methylpropyl)-3-(phenylmethyl)-3H-imidazo-[2,1-b]purin-4(5H)-one;
7,8-Dihydro-2,5-dimethyl-7(R)-(2-methylpropyl)-3-(phenylmethyl)-3H-imidazo-[2,1-b]purin-4(5H)-one;
7,8-Dihydro-2,5-dimethyl-7(R,S)-(methoxycarbonyl)-3-(phenylmethyl)-3H-imidazo[2,1-b]purin-4(5H)-one;
7,8-Dihydro-2,5-dimethyl-7(R,S)-(1-propyl)-3-(phenylmethyl)-3H-imidazo[2,1-b]purin-4(5H)-one;
7,8-Dihydro-2,5-dimethyl-7(S)-(1-methylethyl)-3-(phenylmethyl)-3H-imidazo[2,1-b]purin-4(5H)-one;
7,8-Dihydro-2,5,7,7,8(R,S)-pentamethyl-3H-imidazo[2,1-b]purin-4(5H)-one;
5,7,8,9-Tetrahydro-2,5,7,9(R,S)-pentamethyl-3-(phenylmethyl)-pyrimido[2,1-b]purin-4(3H)-one;
5,6a(R),7,8,9,9a(S)-Hexahydro-2,5-dimethyl-3-(phenylmethyl)cyclopent-[4,5]imidazo[2,1-b]purin-4(3H)-one;
5,6a(S),7,8,9,9a(R)-Hexahydro-2,5-dimethyl-3-(phenylmethyl)cyclopent-[4,5]imidazo[2,1-b]purin-4(3H)-one;
cis-6a,7,8,9,10,10a-Hexahydro-2,5-dimethyl-3-(phenylmethyl)-3H-benzimidazo[2,1-b]purin-4(5H)-one;
5',7'-Dihydro-2',5'-dimethyl-3'-(phenylmethyl)spiro[cyclohexane-1,8-(8H)imidazo[2,1-b]purin]-4-(3'H)-one;
cis-5,6a,7,8,9,9a-Hexahydro-2,5-dimethyl-3-(phenylmethyl)cyclohept-[6,7]imidazo[2,1-b]purin-4(3H)-one;
cis-5,6a,7,8,9,9a-Hexahydro-5-methyl-2-ethyl-3-(phenylmethyl)cyclopent-[4,5]imidazo[2,1-b]purin-4(3H)-one;

cis-6a,7,8,9,10,10a-Hexahydro-5-methyl-2-ethyl-3-(phenylmethyl)-3H-benzimidazo[2,1-b]purin-4-(5H)-one;
cis-5,6a,7,8,9,9a-Hexahydro-5-methyl-2-ethyl-3-(phenylmethyl)cyclopent-[4,5]imidazo[2,1-b]purin-4(3H)-one;
cis-5,6a,7,8,9,9a-Hexahydro-5-methyl-2-phenyl-3-(phenylmethyl)cyclopent-[4,5]imidazo[2,1-b]purin-4(3H)-one;
cis-6a,7,8,9,10,10a-Hexahydro-5-methyl-2-phenyl-3-(phenylmethyl)-3H-benzimidazo[2,1-b]purin-4(5H)-one;
cis-5,6a,7,8,9,9a-Hexahydro-5-methylcyclopenta[4,5]imidazo[2,1-b]purin-4(3H)-one;
cis-5,6a,7,8,9,9a-Hexahydro-2,5-dimethylcyclopenta[4,5]imidazo[2,1-b]purin-4(3H)-one;
cis-5,6a(R), 7,8,9,9a(S)-Hexahydro-2,5-di-methylcyclopent[4,5]imidazo[2,1-b]purin-4(3H)-one;
2',5'-dimethyl-spiro{cyclopentane-1,7'-(8'H)-(3'H)-imidazo[2,1-b]purin}-4'(5'H)-one;
7,8-Dihydro-2,5-dimethyl-7(R)-(1-methylethyl)-3H-imidazo[2,1-b]purin-4(5H)-one;
7,8-Dihydro-2,5,7,7-tetramethyl-3H-imidazo[2,1-b]purin-4(5H)-one;
7,8-Dihydro-2,5-di methyl-7(S)-(1-methylethyl)-3H-imidazo[2,1-b]purin-4(5H)-one;
6a(R),7,8,9,10,10a(S)-Hexahydro-2,5-dimethyl-3H-benzimidazo[2,1-b]purin-4(5H)-one;
5',7'-Dihydro-2',5'-dimethylspiro{cyclohexane-1,7-(8'H)-imidazo[2,1-b]purin}-4'(3'H)-one;
cis-5,6a,7,8,9,9a-Hexahydro-5-methyl-3-(phenylmethyl)cyclopenta[4,5]-imidazo[2,1-b]purin-4(3H)-thione;
5,6a(R),7,8,9,9a(S)-Hexahydro-2,5-dimethyl-3-(phenylmethyl)cyclopent-[4,5]imidazo[2,1-b]purin-4(3H)-thione;
cis-5,6a,7,8,9,9a-Hexahydro-5-methyl-3-(4-chlorophenylmethyl)cyclopenta[4,5]-imidazo[2,1-b]purin-4(3H)-one;
cis-5,6a,7,8,9,9a-Hexahydro-5-methyl-3-(cyclohexylmethyl)cyclopent[4,5]-imidazo[2,1-b]purin-4(3H)-one;
cis-5,6a,7,8,9,9a-Hexahydro-5-methyl-3-(2-naphthylmethyl)cyclopent[4,5]-imidazo[2,1-b]purin-4(3H)-one;
5,6a(R),7,8,9,9a(S)-Hexahydro-2,5-dimethyl-3-(4-bromophenylmethyl)-cyclopent[4,5]imidazo[2,1-b]purin-4(3H)-one;
5,6a(R)-7,8,9,9a(S)-Hexahydro-2,5-dimethyl-3-(4-methoxyphenylmethyl)-cyclopent[4,5]imidazo[2,1-b]purin-4(3H)-one;
cis-5,6a,7,8,9,9a-Hexahydro-2,3,5-trimethylcyclopent[4,5]imidazo[2,1-b]purin-4(3H)-one;
cis-5,6a,7,8,9,9a-Hexahydro-2-(hydroxymethyl)-5-methyl-3-(phenylmethyl)-cyclopent[4,5]imidazo[2,1-b]purin-4(3H)-one;
cis-5,6a,7,8,9,9a-Hexahydro-2-methylthio-5-methyl-3-(Phenylmethyl)cyclopent-[4,5]imidazo[2,1-b]purin-4(3H)-one;
cis-3,4,5,6a,7,8,9,9a-Octahydro-5-methyl-4-oxo-3-(phenylmethyl)cyclopent-[4,5]imidazo[2,1-b]purin-2-carboxylic acid;
cis-3,4,5,6a,7,8,9,9a-Octahydro-5-methyl-4-oxo-3-(phenylmethyl)cyclopent-[4,5]imidazo[2,1-b]purin-2-carboxylic acid, methyl ester;
cis-5,6a,7,8,9,9a-Hexahydro-2-bromo-5-methyl-3-(phenylmethyl)cyclopent[4,5]imidazo[2,1-b]purin-4(3H)one;
cis-5,6a,7,8,9,9a-Hexahydro-2-(methylaminosulfonyl)-5-methyl-3-(phenylmethyl)cyclopent[4,5]imidazo[2,1-b]purin-4(3H)one;
cis-1-Cyclopentyl-5,6a,7,8,9,9a-hexahydro-5-methylcyclopent[4,5]imidazo[2,1-b]purin-4-(1H)one;
cis-5,6a,7,8,9,9a-Hexahydro-3,5-bis-(phenylmethyl)cyclopent(4,5)imdazo[2,1-b]purin-4(3H)-one;
cis-6a,7,8,9,10,10a-Hexahydro-3,5-bis-(phenylmethyl)-3H-benzimidazo[2,1-b]purin-4(5H)one;
cis-3-Cyclopentyl-5,6a,7,8,9,9a-hexahydro-5-methylcyclopent[4,5]imidazo[2,1-b]purin-4(3H)one;
5'-Methyl-3'-(phenylmethyl)spiro[cyclopentane-1,7-(8'H)-(3'H)imdazo[2,1-b]purin]-4-(5H)one;
2',5'-Dimethyl-3'-(phenylmethyl)-spiro[cyclopentane-1,7-(8'H)-(3'H)imdazo[2,1-b]purin]-4-(5'H)one;
cis-5,6a(R)7,8,9,9a(S)-Hexahydro-5-methyl-3-(phenylmethyl)cyclopent[4,5]-imidazo[2,1-b]purin-4(3H)one;
cis-3-Cyclopentyl-5,6a,7,8,9,9a-Hexahydro-2,5-dimethylcyclopent[4,5]imidazo-[2,1-b]purin-4(3H)one;
5'-Methyl-2'-trifluoromethyl-3'-(phenylmethyl)spiro{cyclopentane-1,7'(8'H)-(3'H)imdazo[2,1-b]purin}-4-(5'H)-one;
7,8-Dihydro-5,7,7-trimethyl-2-trifluoromethyl-3-(phenylmethyl)-3H-imidazo[2,1-b]purin-4(5H)-one;
(+/−)-cis-5,6a,7,8,9,9a-Hexahydro-5-methyl-2-trifluoromethyl-3-(phenylmethyl)-cyclopent[4,5]imidazo[2,1-b]purin-4(3H)-one;
(+/−)-6a,7,8,9,9a,10,11,11a-Octahydro-2,5-dimethyl-3-(phenylmethyl)-3H-pentaleno[6a',1':4,5]imidazo[2,1-b]purin-4(5H)-one;
(+)-6a,7,8,9,9a,10,11,11a-Octahydro-2,5-dimethyl-3-phenylmethyl-3H-pentaleno[6a',1':4,5]imidazo[2,1-b]purin-4(5H)-one;
(−)-6a,7,8,9,9a,10,11,11a-Octahydro-2,5-dimethyl-3-phenylmethyl-3H-pentaleno[6a',1':4,5]Imidazo[2,1-b]purin-4(5H)-one;
(+/−)6a,7,8,9,9a,10,11,11a-Octahydro-2,5-dimethyl-3H-pentaleno[6a',1':4,5]-imidazo[2,1-b]purin-4(5H)-one;
(+)-6a,7,8,9,9a,10,11,11a-Octahydro-2,5-dimethyl-3H-pentaleno[6a',1':4,5]-imidazo[2,1-b]purin-4(5H)-one;
(−)-6a,7,8,9,9a,10,11,11a-Octahydro-2,5-dimethyl-3H-pentaleno[6a',1':4,5]-imidazo[2,1-b]purin-4(5H)-one;
6a,7,8,9,10,10a,11,12,13,13a-Decahydro-2,5-dimethyl-(3-phenylmethyl)-napth[1,8a-d]imidazo[2,1-b]purin-4(5H)one;
7(R)-Cyclohexyl-7,8-dihydro-2,5-dimethyl-3-(phenylmethyl)-3H-imidazo[2,1-b]purin-4(3H)-one;
7(R)-Cyclohexyl-7,8-dihydro-2,5-dimethyl-3H-imidazo[2,1-b]purin-4(5H)-one;
7(S)-Cyclohexyl-7,8-dihydro-2,5-dimethyl-3-(phenylmethyl)-3H-imidazo[2,1-b]purin-4(3H)-one;
7(S)-Cyclohexyl-7,8-dihydro-2,5-dimethyl-3H-imidazo[2,1-b]purin-4(5H)-one;
5,6a(R),7,8,9,9a(S)-Hexahydro-2,5-dimethyl-[3-(trimethylacetoxy)methyl]-cyclopent[4,5]imidazo[2,1-b]purin-4(3H)-one;
5,6a(R),7,8,9,9a(S)-Hexahydro-2,5-dimethyl-3-(4-pyridylmethyl)cyclopent-[4,5]imidazo[2,1-b]purin-4(3H)-one;
5,6a(R),7,8,9,9a(S)-Hexahydro-2,5-dimethyl-3-[2-(4-morpholinyl)-ethyl]cyclopent[4,5]imidazo[2,1-b]purin-4(3H)-one;
5,6a(R),7,8,9,9a(S)-Hexahydro-2,5-dimethyl-3-[acetoxymethyl]cyclopent-[4,5]imidazo[2.1-b]purin-4(3H)-one;
5,6a,7,8,9,9a-Hexahydro-2,5,6a-trimethyl-3-(phenylmethyl)cyclopent-[4,5]imidazo[2,1-b]purin-4(3H)-one;
5,6a(R),7,8,9,9a(S)-Hexahydro-2,5,6a-trimethyl-3-(phenylmethyl)-cyclopent[4,5]imidazo[2,1-b]purin-4(3H)-one;
5,6a(S),7,8,9,9a(R)-Hexahydro-2,5,6a-trimethyl-3-(phenylmethyl)-cyclopent[4,5]imidazo[2,1-b]purin-4(3H)-one;
cis-6a,7,8,9,10,10a-Hexahydro-2,5,7-trimethyl-3-(phenylmethyl)-3H-benzimidazo[2,1-b]purin-4(5H)-one;
cis-5,6a,7,8,9,9a-Hexahydro-2,5,6a-trimethylcyclopent[4,5]imidazo[2,1-b]purin-4(3H)-one; or
cis-[6a,7,8,9,10,10a-Hexahydro-2,5,7-trimethyl-3H-benzimidazo[2,1-b]purin-4(5H)-one].

In another embodiment, the PDE 1 Inhibitors for use in the methods of treatment described herein are Compounds of Formula IXa or IXb

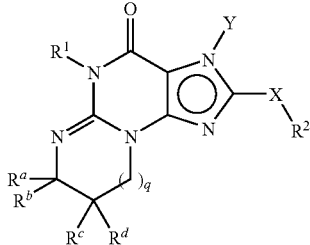

Formula IXa

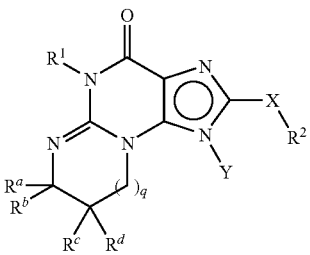

Formula IXb or a pharmaceutically acceptable salt thereof, wherein,
q=0 or 1;
$R^1$ is H, cycloalkyl, alkyl, $R^{23}$-alkyl- or $R^{26}$;
$R^a$, $R^b$ and $R^c$ are, independently of one another, each H, alkyl, cycloalkyl, aryl, $R^{22}$-aryl- or $R^{24}$-alkyl-; or
$R^a$ and $R^b$, together with the carbon to which they are both attached, form a 4- to 7-membered ring, and $R^c$ is H or alkyl; or
$R^a$ and $R^c$, together with the respective carbons to which they are attached, form a 4- to 7-membered ring, and $R^b$ is H or alkyl;
 (i) X is a bond;
 Y is aryl-alkyl or $R^{22}$-aryl-alkyl-; and
 $R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-;
 (ii) X is a bond;
 Y is aryl-alkyl or $R^{22}$-aryl-alkyl-; and
 $R^2$ is H, halo, —CONHR$^6$, —CONR$^6$R$^7$, —CO$_2$R$^6$, monohaloalkyl, polyhaloalkyl, azido, cyano, —C=N—OR$^6$, cycloalkyl, cycloalkylalkyl, $R^{26}$, aminosulfonyl, alkyl or $R^{23}$-alkyl-
 (iii) X is —O— or —S—;
 Y is aryl-alkyl or $R^{22}$-aryl-alkyl-; and
 $R^2$ is $R^{26}$, cycloalkyl cycloalkylalkyl, heterocycloalkyl, cycloalkenyl or $R^{26}$-alkyl-;
 (iv) X is —O— or —S—;
 Y is aryl-alkyl or $R^{22}$-aryl-alkyl-; and
 $R^2$ is alkyl, $R^{26}$, cycloalkyl, cycloalkylalkyl, heterocycloalkyl, cycloalkenyl or $R^{28}$-alkyl-;
 (v) X is —SO— or —SO$_2$—;
 Y is aryl-alkyl or $R^{22}$-aryl-alkyl-; and
 $R^2$ is alkyl, $R^{26}$, cycloalkyl, cycloalkylalkyl, heterocycloalkyl, cycloalkenyl or $R^{28}$-alkyl-;
 (vi) X is —NR$^8$—;
 Y is aryl-alkyl or $R^{22}$-aryl-alkyl-; and
 $R^2$ is $(R^{29})_p$-alkyl-, cycloalkyl, $(R^{30})_p$-cycloalkyl-, cycloalkenyl,
 $(R^{30})_p$-cycloalkenyl-, heterocycloalkyl or $(R^{30})_p$-heterocycloalkyl-:
 (vii) X is —NR$^8$—;
 Y is aryl-alkyl or $R^{22}$-aryl-alkyl-; and
 $R^2$ is alkyl, $R^{26}$, cycloalkyl, cycloalkylalkyl, heterocycloalkyl, cycloalkenyl or $R^{31}$-alkyl-; or (viii) X is —C≡C—;
 Y is aryl-alkyl or $R^{22}$-aryl-alkyl-; and
 $R^2$ is alkyl, $R^{26}$, cycloalkyl, cycloalkylalkyl or $R^{23}$-alkyl-;
where,
 $R^6$ is H or $R^7$;
 $R^7$ is alkyl, cycloalkyl or cycloalkylalkyl;
 $R^8$ is heterocycloalkyl or $R^6$;
 $R^{21}$ is 1-6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cycloalkyl, cycloalkylalkyl, amino, alkylamino, acylamino, carboxyl, —C(O)OR$^{34}$, carboxamido, —OCF$_3$ and acyloxy;
 $R^{22}$ is 1-6 substituents each independently selected from the group consisting of alkyl and $R^{21}$;
 $R^{23}$ is cycloalkoxy aryloxy, alkylthio, arylthio, cycloalkyl or $R^{28}$;
 $R^{24}$ is cycloalkyl or $R^{26}$;
 $R^{25}$ is hydroxy, alkoxy, amino, monoalkylamino, dialkylamino or $R^{26}$;
 $R^{26}$ is aryl, $R^{22}$-aryl-, heteroaryl or $R^{22}$-heteroaryl-;
 $R^{27}$ is cycloalkoxy, aryloxy, alkylthio, arylthio, heteroaryl, $R^{22}$-heteroaryl-, cycloalkyl, heterocycloalkyl, cycloalkenyl, cycloalkylamino or heterocycloalkylamino;
 $R^{28}$ is cycloalkylamino, heterocycloalkylamino or $R^{25}$;
 $R^{29}$ is alkoxy, cycloalkylamino, heterocycloalkylamino or $R^{26}$;
 $R^{30}$ is halo, hydroxy, alkoxy, amino, aminosulfonyl, cyano, monohaloalkyl, polyhaloalkyl, thiol, alkylthio, alkyl, cycloalkyl, cycloalkylalkyl or acyloxy;
 $R^{31}$ is cycloalkyl or $R^{28}$;
 $R^{34}$ is alkyl, aryl, aralkyl and heteroaryl; and
 p is 1 to 4.
6.1 The invention further provides the use of PDE 1 Inhibitors of Formula IXa or IXb, in free or salt form, selected from the following:

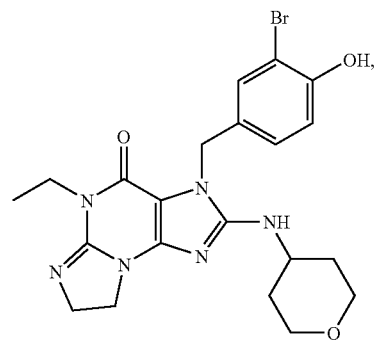

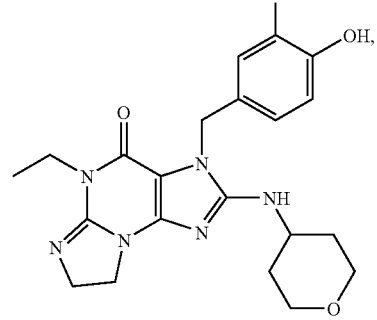

23
-continued
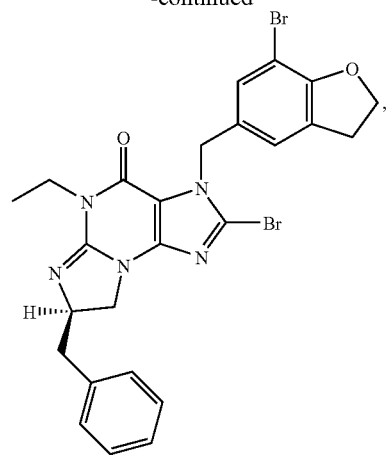
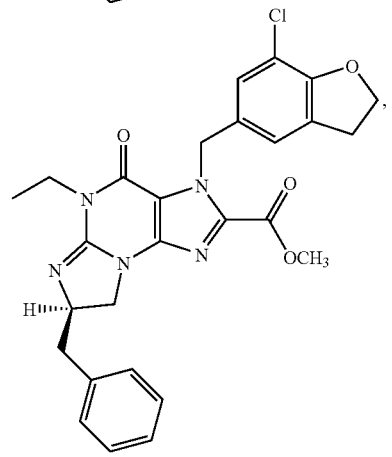
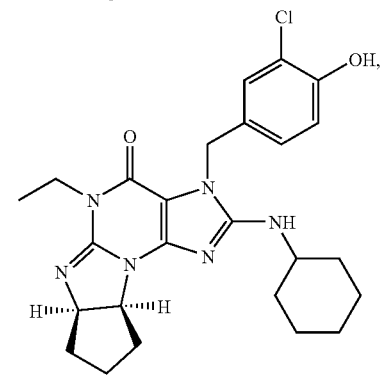
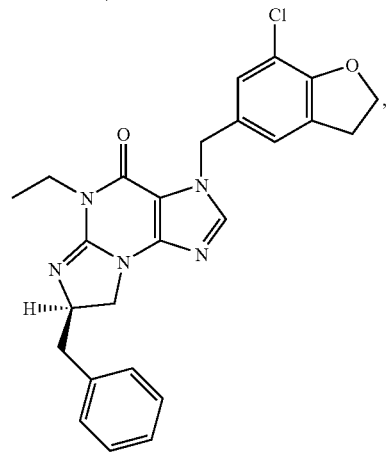
24
-continued
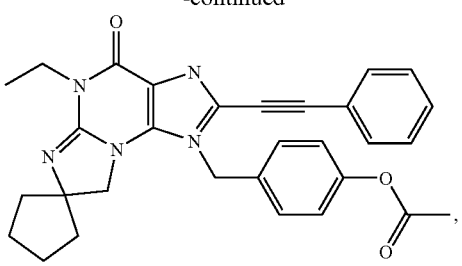
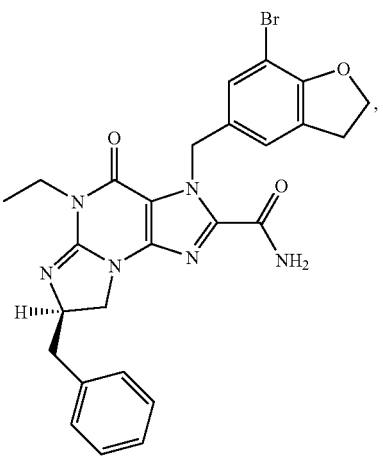
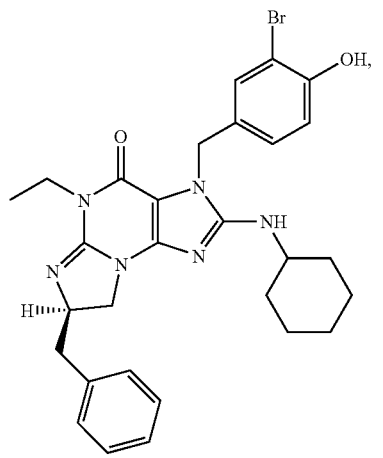
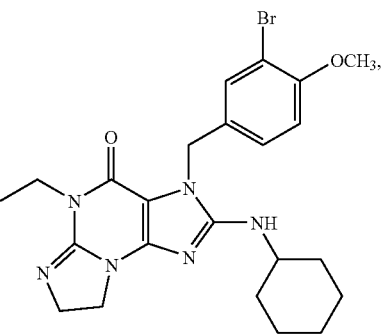

25
-continued
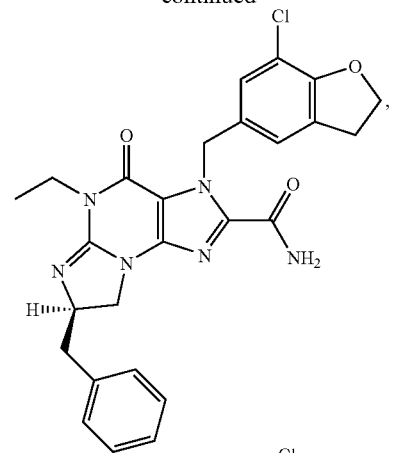
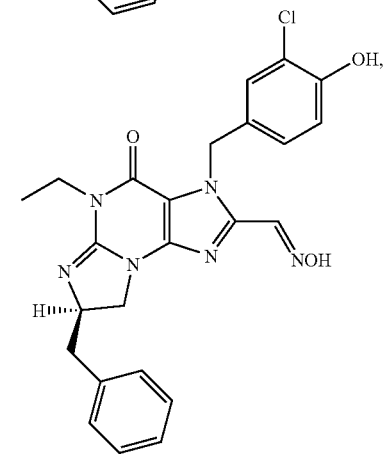
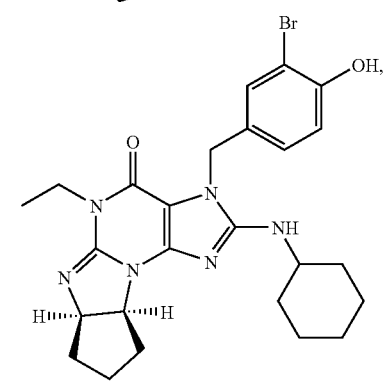
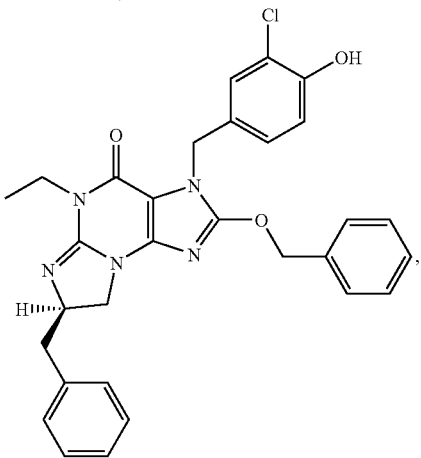
26
-continued
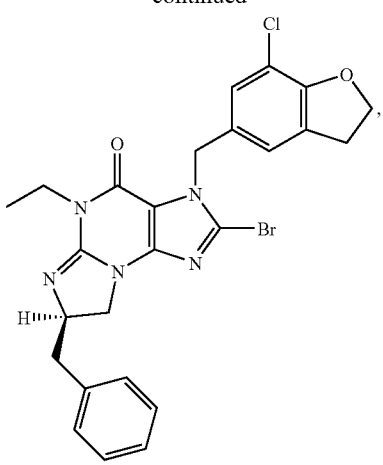
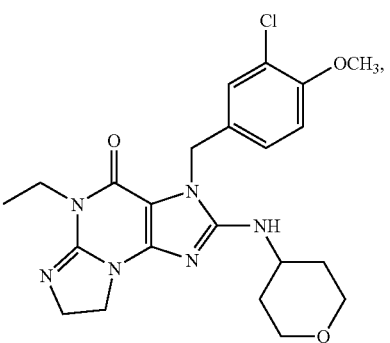
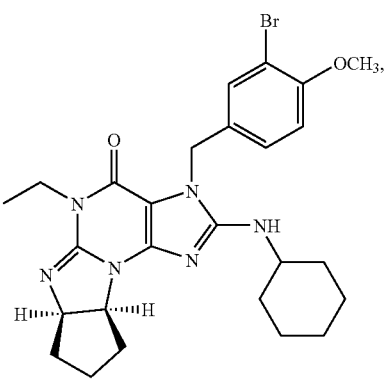
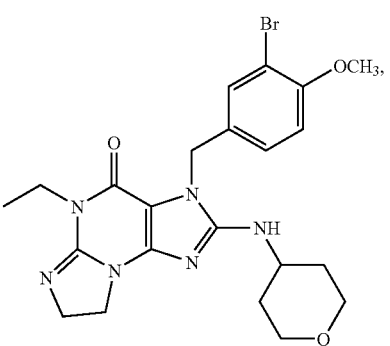

-continued
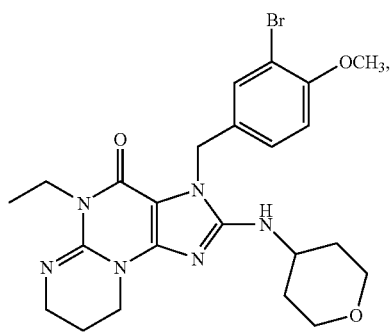
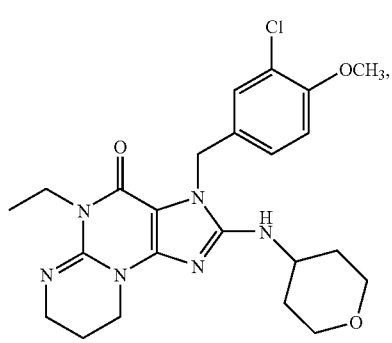
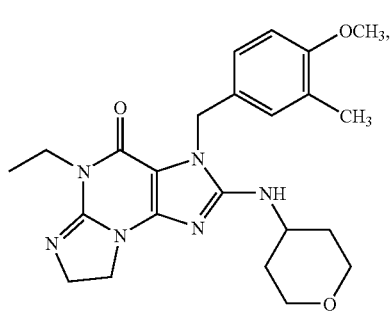
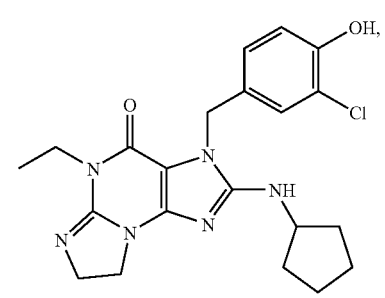
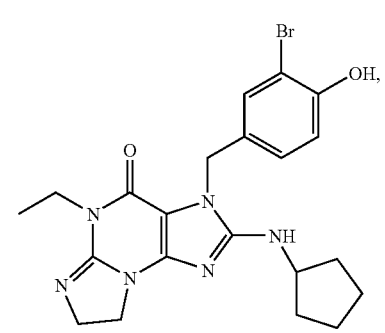
-continued
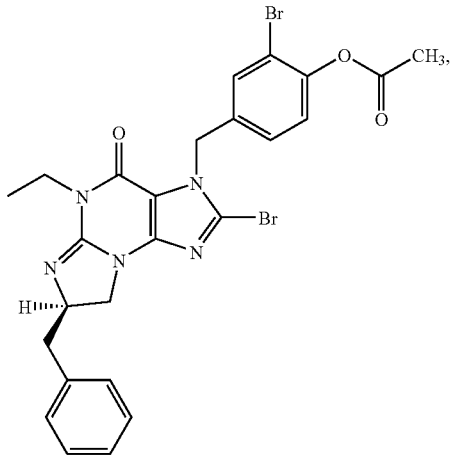
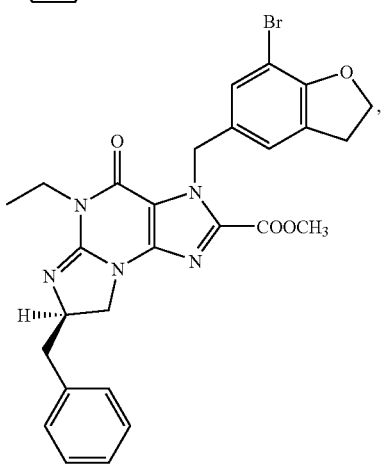
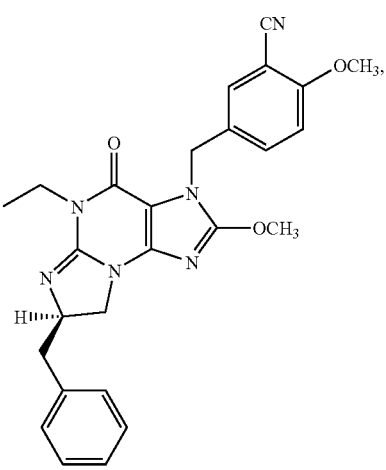
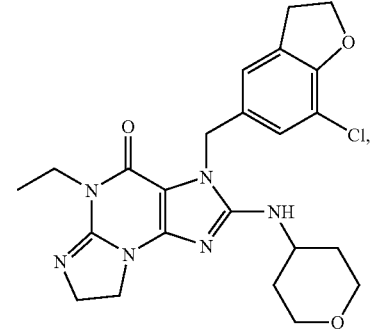

-continued

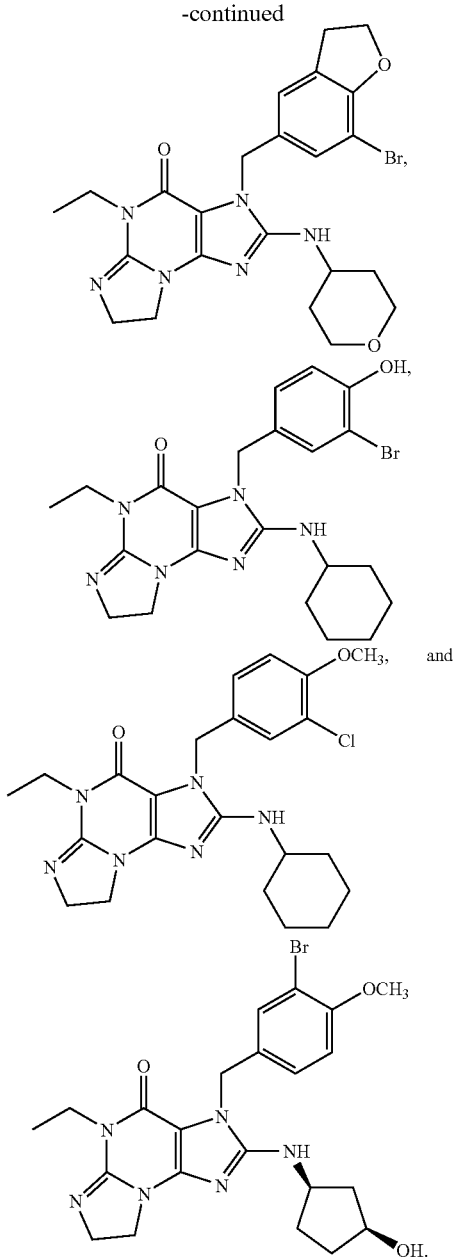

In another embodiment, the invention provides the use of PDE 1 Inhibitors of Formula X:

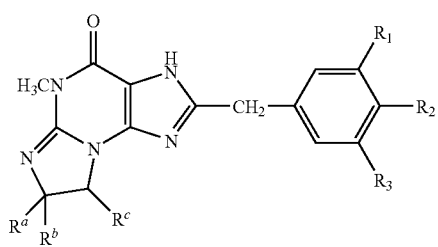

Formula X in free or a pharmaceutically acceptable salt thereof, wherein: $R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring; and $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons.

In a further embodiment, the invention provides the use of PDE 1 Inhibitors of Formula X as follows:

7.1 Formula X, wherein $R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring;

7.2 Formula X or 7.1, wherein $R_1$ is H, methoxy or trifluoromethyl;

7.3 Formula X or 7.1 or 7.2, wherein $R_1$ is H;

7.4 Formula X or any of 7.1-7.3, wherein $R_2$ is selected from a group consisting of H, halo (e.g., F, Cl), methoxy, methyl, trifluoromethyl, dimethylamino, phenyl, methoxyphenyl-, —$OCF_3$, 3,4-$OCH_2O$—, pyrrolidin-1-yl, pyrol-1-yl and morpholin-4-yl;

7.5 Formula X or any of 7.1-7.4, wherein $R_1$ and $R_2$ together with the carbon atoms to which they are attached form a benzene ring;

7.6 Formula X or any of 7.1-7.5, wherein $R_3$ is H or methoxy;

7.7 Formula X or any of 7.1-7.6, wherein $R_3$ is H, 7.8 Formula X or any of 7.1-7.7, wherein $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons;

7.9 Formula X or any of 7.1-7.8, wherein $R^a$ is hydrogen and $R^b$ and $R^c$ together with the carbon atoms to which they are attached, form a saturated ring of 5 carbons, and wherein $R_1$, $R_2$ and $R_3$ are as defined in the following table

| $R_1$ | $R_2$ | $R_3$ |
|---|---|---|
| H | H | H |
| —$OCH_3$ | H | H |
| H | F | H |
| H | —$OCH_3$ | H |
| H | OH | H |
| H | —$CH_3$ | H |
| H | $(CH_3)_2N$— | H |
| —$OCH_3$ | —$OCH_3$ | —$OCH_3$ |

-continued

| $R_1$ | $R_2$ | $R_3$ |
|---|---|---|
| —OCH₃ | —OCH₃ | H |
| —CF₃ | H | H |
| H | C₆H₅— | H |
| H | —OCF₃ | H |
| H | —N(pyrrolidine) | H |
| H | —N(pyrrole) | H |
| 3,4-OCH₂O— | | H |
| H | —N(morpholine) | H |
| H | (tolyl-OCH₃) | H |
| $R_1$ and $R_2$, together with the carbon atoms to which they are attached form a benzene ring | | H |
| H | Cl | H. |

7.10 Formula X or any of 7.1-7.9, selected from a group consisting of

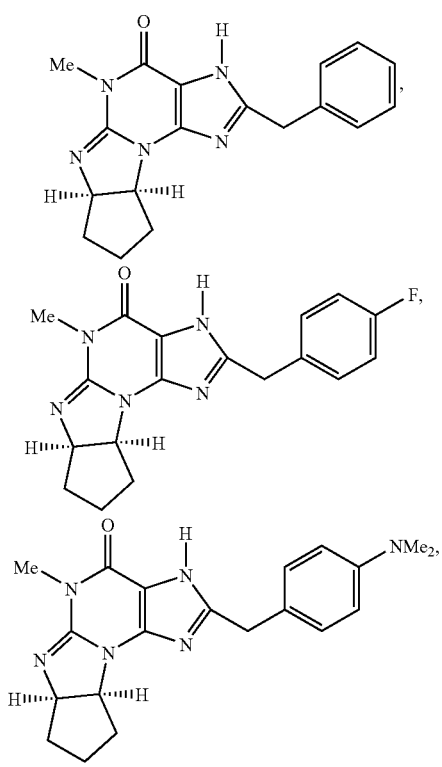

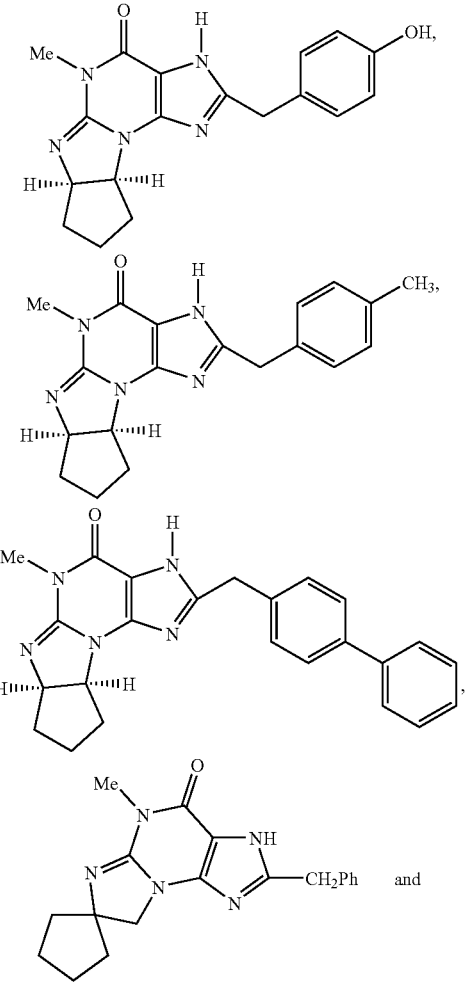

7.11 Formula X or any of 7.1-7.9, selected from a group consisting of:
2'-benzyl-5'-methyl-spiro[cyclopentane-1',7'(8'H)-[3'H]-imidazo[2,1-b]purin]-4'-(5'H)-one;
2'-benzyl-5,7,7-trimethyl-3H-imidazo[2,1-b]purin-4-(5H)-one;
(+)-2-benzyl-7,8-dihydro-5-methyl-7-(1-methylethyl)-1H-imidazo[2,1-b]-purin-4(5H)-one;
(+,−)-6a,7,8,9,9a,10,11,11a-octahydro-5-methyl-2-(3,4-methylene-dioxyphenylmethyl)-3H-pentalen[6a, 1:4,5]imidazo[2,1-b]purin-4(5H)-one; and
(+)-cis-6a,7,9,9a-tetrahydro-5-methyl-2-[4-(trifluoromethyl)-phenylmethyl]-3H-furo[3',4':4,5]imidazo[2,1-b]purin-4(5H)-one,
in free or salt form.

7.12 Formulae X or 7.1-7.11, wherein the compounds inhibit phosphodiesterase-mediated (e.g., PDE1-mediated, especially PDE1B-mediated) hydrolysis of cGMP, e.g., with an IC$_{50}$ of less than 1 μM, preferably less than 25 nM in an immobilized-metal affinity particle reagent PDE assay, for example, as described in Example 1;

In another embodiment, the invention provides the use of PDE 1 Inhibitors selected from the following:

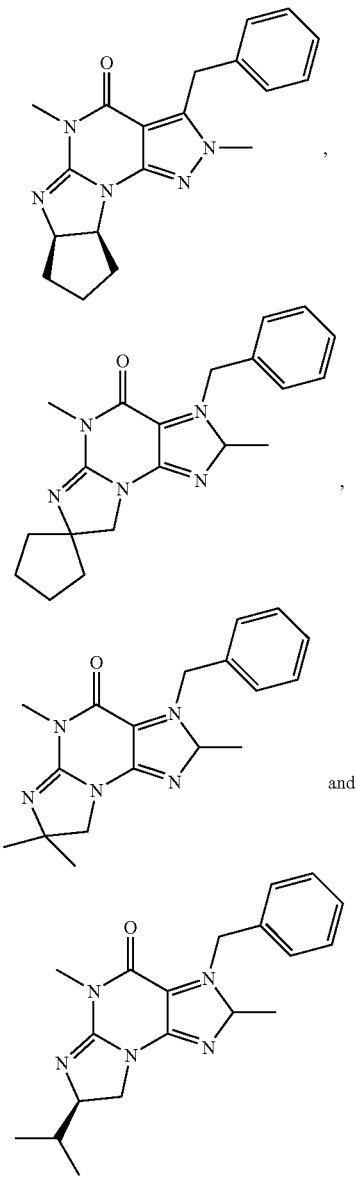

and in free or salt form (Formula XI).

If not otherwise specified or clear from context, the following terms as used herein have the following meetings:

a. "Alkyl" as used herein is a saturated or unsaturated hydrocarbon moiety, preferably saturated, preferably one to seven carbon atoms in length, which may be linear or branched, and may be optionally substituted, e.g., mono-, di-, or tri-substituted, e.g., with halogen (e.g., chloro or fluoro), hydroxy, or carboxy.

b. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.

c. "Heterocycloalkyl" as used herein is a saturated or unsaturated nonaromatic hydrocarbon moiety, preferably saturated, preferably comprising three to nine carbon atoms, at least one atom selected from a group consisting of N, O or S, at least some of which form a nonaromatic mono- or bicyclic, or bridged cyclic structure, and which may be optionally substituted, e.g., with halogen (e.g., chloro or fluoro), hydroxy, or carboxy. Examples of heterocycloalkyl include pyrrolidinyl (e.g., pyrrolidin-1-yl), morpholinyl (e.g., morpholin-4-yl), d. "Aryl" as used herein is a mono or bicyclic aromatic hydrocarbon (e.g., phenyl, naphthyl), preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

e. "Heteroaryl" as used herein is an aromatic moiety wherein one or more of the atoms making up the aromatic ring is sulfur or nitrogen rather than carbon, e.g., pyridyl, thiadiazolyl, pyrrolyl (e.g., pyrrol-2-yl) or imidazolyl (e.g., 1H-imidazol-2-yl), which may be optionally substituted, e.g., with alkyl, halogen, haloalkyl, hydroxy or carboxy.

PDE 1 Inhibitors may exist in free or salt form, e.g., as acid addition salts. In this specification unless otherwise indicated language such as PDE 1 Inhibitors is to be understood as embracing the compounds in any form, for example free or acid addition salt form, or where the compounds contain acidic substituents, in base addition salt form. The PDE 1 Inhibitors are intended for use as pharmaceuticals, therefore pharmaceutically acceptable salts are preferred. Salts which are unsuitable for pharmaceutical uses may be useful, for example, for the isolation or purification of free PDE 1 Inhibitors or their pharmaceutically acceptable salts.

PDE 1 Inhibitors may in some cases also exist in prodrug form, for example when the compounds contain physiologically hydrolysable and acceptable esters. As used herein, "physiologically hydrolysable and acceptable ester" means esters of PDE 1 Inhibitors which are hydrolysable under physiological conditions to yield acids (in the case of PDE 1 Inhibitors which have hydroxy substituents) or alcohols (in the case of PDE 1 Inhibitors which have carboxy substituents) which are themselves physiologically tolerable at doses to be administered. As will be appreciated the term thus embraces conventional pharmaceutical prodrug forms.

Methods of making and formulating the PDE 1 Inhibitors, novel intermediates useful for making PDE 1 Inhibitors, and methods of using the PDE 1 Inhibitors for treatment of diseases are generally disclosed in EP 0201188 (or U.S. Pat. No. 4,666,908) and EP 0911333 (or U.S. Pat. No. 6,235,742); PCT/US2006/022066; PCT/US2006/033179; WO 03/042216 (U.S. Pat. No. 6,943,171); U.S. Pat. No. 6,969,719; U.S. Pat. No. 5,939,419; EP 0 538 332 (U.S. Pat. No. 5,393,755); Xia et al., *J. Med. Chem.* (1997), 40, 4372-4377 and Ahn et al., *J. Med. Chem.* (1997), 40, 2196-2210, the contents of each of which are incorporated herein by reference by their entirety.

Methods of Treatment

The invention provides methods of enhancing progesterone signaling in a human or animal patient suffering from disorders that may be ameliorated by said enhancement comprising administering an effective amount of a PDE 1 inhibitor, e.g., a PDE 1 Inhibitor as hereinbefore described, for example a Compound of Formula I, Ia, II, III, IV, V, VIIa, VIIb, VIIIa, VIIIb, IXa, IXb, or any of Formulae 1.2-1.17, 2.1-2.9, 3.2-3.22, 4.1-4.16, 5.1-5.6 to a human or animal patient, preferably a human, in need thereof. PDE 1 inhibitors of said method also include Compound of Formula X or XI or any of 6.1 or 7.1-7.12.

Disorders that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function.

The PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma.

The methods of the invention are also useful for animal breeding, for example to induce sexual receptivity and/or estrus in a nonhuman female mammal to be bred.

PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of
  (i) a PDE 1 Inhibitor, e.g., of Formula I, Ia, II, III, IV, V, VIIa, VIIb, VIIIa, VIIIb, IXa or IXb or any of Formulae 1.2-1.17, 2.1-2.9, or 3.2-3.22, 4.1-4.16, 5.1-5.6;
  (ii) a hormone, e.g., selected from estrogen and estrogen analogues (e.g., estradiol, estriol, estradiol esters) and progesterone and progesterone analogues (e.g., progestins)
to a patient in need thereof.

The invention also comprises a method of treating disorders that may be ameliorated by enhancement of progesterone signaling comprising administering simultaneously, sequentially, or contemporaneously administering therapeutically effective amounts of sss
  (i) a PDE 1 Inhibitor, e.g., of Formula X or XI or any of 6.1 or 7.1-7.12;
  (ii) a hormone, e.g., selected from estrogen and estrogen analogues (e.g., estradiol, estriol, estradiol esters) and progesterone and progesterone analogues (e.g., progestins)
to a patient in need thereof.

The present invention also provides
  (i) a PDE 1 Inhibitor for use in the treatment of any disease or condition as hereinbefore set forth, or in a method of treatment as hereinbefore set forth;
  (ii) the use of a PDE 1 Inhibitor in the manufacture of a medicament for treating a disease or condition as hereinbefore set forth, or manufacture of a medicament for use in a method of treatment as hereinbefore set forth; and
  (iii) a pharmaceutical composition comprising a PDE 1 Inhibitor in combination or association with a pharmaceutically acceptable diluent or carrier for use in the treatment of a disease or condition as hereinbefore set forth, or for use in a method of treatment as hereinbefore set forth.

The words "treatment" and "treating" are to be understood accordingly as embracing treatment or amelioration of any of the symptoms of disease as well as treatment of the cause of the disease.

The term "enhanced progesterone signaling" refers to an enhanced activation and/or phosphorylation of progesterone receptors compared to a reference. Enhancement of progesterone signaling may be measured by intracellular cAMP or cGMP levels or DARRP-32 phosphorylation, or by analyzing the lordosis response in an animal model in the presence and absence of PDE1 inhibitor, wherein increases in lordosis response compared to the response in a female mammal in the absence of the PDE1 inhibitor is indicative of enhanced progesterone signaling.

The term "female sexual dysfunction" is known in the art and generally refers to the impairment of the sexual function. For example, female sexual dysfunction may refer to conditions or disorders wherein the female patients experience symptoms including, but not limited to low, decreased or lack of receptivity to sexual activities, low or lack of sexual arousal, painful intercourse, and infrequent or lack of sexual climax.

The term "patient" herein refers to male, female or intersexual or transsexual male or female.

Dosages employed in practicing the present invention will of course vary depending, e.g. on the particular disease or condition to be treated, the particular PDE 1 Inhibitor used, the mode of administration, and the therapy desired. PDE 1 Inhibitors may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a PDE 1 Inhibitor, together with a pharmaceutically acceptable diluent or carrier therefor.

Pharmaceutical compositions comprising PDE 1 Inhibitors may be prepared using conventional diluents or excipients and techniques known in the galenic art. Thus oral dosage forms may include tablets, capsules, solutions, suspensions and the like.

EXAMPLES

1. Measurement of PDE1B Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaxCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

Example 2

PDE 1 Inhibitor Effect on Sexual Response in Female Rats

The effect of PDE1 inhibitors on Lordosis Response in female rats is measured as described in Mani, et al., Science (2000) 287: 1053. Ovariectomized and cannulated wild-type rats are primed with 2 μg estrogen followed 24 hours later by intracerebroventricular (icv) injection of progesterone (2 μg), PDE1 inhibitors of the present invention (0.1 mg and 2.5 mg) or sesame oil vehicle (control). The rats are tested for lordosis response in the presence of male rats. Lordosis response is quantified by the lordosis quotient (LQ=number of lordosis/10 mounts×100). The LQ for estrogen-primed female rats receiving compounds 1 or 2, even at 0.1 mg, is over 75, similar to estrogen-primed rats receiving progesterone and significantly higher (p<0.001) than for estrogen-primed rats receiving vehicle.

What is claimed is:

1. A method of treatment of female sexual dysfunction, wherein the female sexual dysfunction is ameliorated by enhancement of progesterone signaling pathways, comprising administering an effective amount of a PDE 1 inhibitor to a patient in need thereof, wherein the PDE 1 inhibitor is a compound of formula (I)

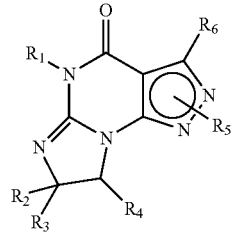

Formula I wherein
(i) $R_1$ is H or $C_{1-4}$ alkyl;
(ii) $R_4$ is H or $C_{1-4}$ alkyl and $R_2$ and $R_3$ are, independently, H or $C_{1-4}$ alkyl, aryl, heteroaryl, heteroarylalkoxy, arylalkoxy, heteroarylalkyl, or arylalkyl;
or $R_2$ is H and $R_3$ and $R_4$ together form a di-, tri-, or tetra-methylene bridge;
(iii) $R_5$ is attached to one of the nitrogens on the pyrazolo portion of Formula I and is a substituted heteroarylalkyl or is a moiety of Formula Q

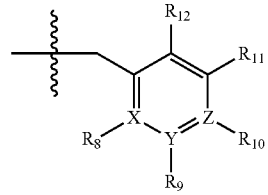

Formula Q wherein X, Y and Z are, independently, N or C, wherein only one of X, Y, of Z is N; $R_8$, $R_9$, $R_{11}$ and $R_{12}$ are independently H or halogen; and $R_{10}$ is haloalkyl, phenyl, pyridyl, or thiadiazolyl; provided that when X, Y, or Z is nitrogen, $R_8$, $R_9$, or $R_{10}$, respectively, is not present; and
(iv) $R_6$ is phenylamino or benzylamino;
wherein
phenyl is optionally substituted with $C_{1-4}$ alkyl, halogen, halo$C_{1-4}$alkyl, hydroxyl, $C_{1-4}$carboxy or an additional aryl or heteroaryl; or pyridyl or thiadiazolyl is optionally substituted with C$_{1-4}$alkyl, halogen, haloC$_{1-4}$alkyl, hydroxyl or C$_{1-4}$carboxy;

in free or salt form.

2. The method according to claim 1 wherein the PDE 1 inhibitor is a compound of Formula III

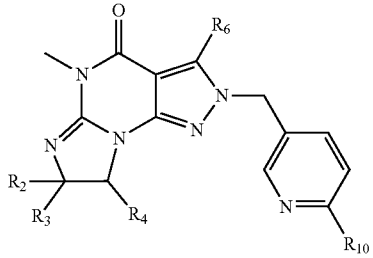

Formula III wherein

R$_2$ is H and R$_3$ and R$_4$ together form a tri- or tetra-methylene bridge; or at least one of R$_2$ and R$_3$ is methyl, isopropyl or arylalkoxy and R$_4$ is H; or R$_2$ and R$_3$ are H and R$_4$ is a C$_{1-4}$ alkyl;

R$_6$ is phenylamino or benzylamino;

R$_{10}$ is haloalkyl, phenyl, pyridyl, or thiadiazolyl;

wherein phenyl is optionally substituted with C$_{1-4}$ alkyl, halogen, haloC$_{1-4}$alkyl, hydroxyl, C$_{1-4}$carboxy or an additional aryl or heteroaryl; or pyridyl or thiadiazolyl is optionally substituted with C$_{1-4}$alkyl, halogen, haloC$_{1-4}$alkyl, hydroxyl or C$_{1-4}$carboxy;

in free or salt form.

3. The method according to claim 1 wherein the PDE 1 inhibitor is a compound of Formula IV

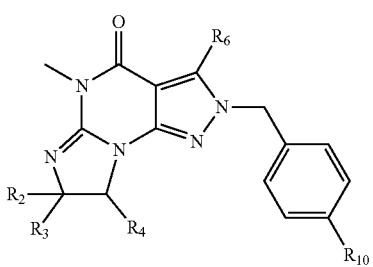

Formula IV wherein

R$_2$ is H and R$_3$ and R$_4$ together form a tri- or tetra-methylene bridge; or at least one of R$_2$ and R$_3$ is methyl, isopropyl or arylalkoxy and R$_4$ is H; or R$_2$ and R$_3$ are H and R$_4$ is a C$_{1-4}$ alkyl;

R$_6$ is phenylamino or benzylamino;

R$_{10}$ is phenyl, pyridyl, or thiadiazolyl;

wherein phenyl is optionally substituted with C$_{1-4}$ alkyl, halogen, haloC$_{1-4}$alkyl, hydroxyl, C$_{1-4}$carboxy or an additional aryl or heteroaryl; or pyridyl or thiadiazolyl is optionally substituted with C$_{1-4}$alkyl, halogen, haloC$_{1-4}$alkyl, hydroxyl or C$_{1-4}$carboxy;

in free or salt form.

4. The method according to claim 1 wherein the PDE 1 inhibitor is a compound of formula Ia

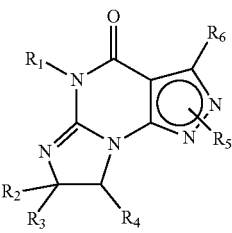

Formula Ia wherein (i) R$_1$ is H or C$_{1-4}$ alkyl;

(ii) R$_4$ is H and R$_2$ and R$_3$ are, independently, H or C$_{1-4}$ alkyl, aryl, or arylalkyl;

or R$_2$ is H and R$_3$ and R$_4$ together form a di-, tri- or tetramethylene bridge;

(iii) R$_5$ is attached to one of the nitrogens on the pyrazolo portion of formula Ia and is a substituted benzyl of formula B

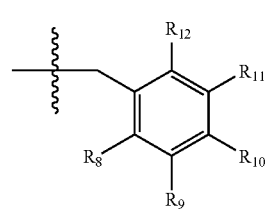

Formula B wherein R$_8$, R$_9$, R$_{11}$ and R$_{12}$ are independently H or halogen; and R$_{10}$ is haloalkyl, phenyl, pyridyl, or thiadiazolyl R$_6$ is phenylamino or benzylamino;

wherein phenyl is optionally substituted with C$_{1-4}$ alkyl, halogen, haloC$_{1-4}$alkyl, hydroxyl, C$_{1-4}$carboxy or an additional aryl or heteroaryl; or pyridyl or thiadiazolyl is optionally substituted with C$_{1-4}$alkyl, halogen, haloC$_{1-4}$alkyl, hydroxyl or C$_{1-4}$carboxy in free or salt form.

5. The method according to claim 1 wherein the PDE 1 inhibitor is a compound of Formula VI

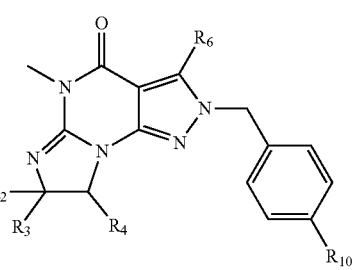

Formula VI wherein

R$_2$ is H and R$_3$ and R$_4$ together form a tri- or tetra-methylene bridge; or R$_2$ and R$_3$ are each methyl and R$_4$ is H; or R$_2$ and R$_4$ are H and R$_3$ is isopropyl;

$R_6$ is phenylamino or benzylamino;
$R_{10}$ is phenyl, pyridyl, or thiadiazolyl;
wherein
phenyl is optionally substituted with $C_{1-4}$ alkyl, halogen, halo$C_{1-4}$alkyl, hydroxyl, $C_{1-4}$carboxy or an additional aryl or heteroaryl; or
pyridyl or thiadiazolyl is optionally substituted with $C_{1-4}$alkyl, halogen, halo$C_{1-4}$alkyl, hydroxyl or $C_{1-4}$carboxy in free or salt form.

6. The method according to claim 1 wherein the compound inhibits phosphodiesterase-mediated hydrolysis of cGMP or cAMP.

7. The method according to claim 1 wherein the PDE1 inhibitor is a PDE1B inhibitor.

8. The method according to claim 1 further comprising administering hormone replacement therapy to the patient.

9. The method according to claim 8, wherein hormone replacement therapy comprises administration of a hormone selected from estrogen, estradiol, estriol, estradiol esters, progesterone and progestins.

10. The method according to claim 1, wherein said patient is further suffering from a physiological disorder, symptom or disease selected from a group consisting of exercise amenorrhoea, anovulation, menopause, menopausal symptoms, hypothyroidism, pre-menstrual syndrome, premature labor, infertility, irregular menstrual cycles, abnormal uterine bleeding, osteoporosis, autoimmune disease, multiple sclerosis, estrogen-induced endometrial hyperplasia and estrogen-induced endometrial carcinoma.

11. The method according to claim 1, wherein said patient is a human.

12. The method according to claim 1 wherein the female sexual dysfunction is a lack of receptivity to mating in a nonhuman female mammal.

13. The method according to claim 1 wherein the PDE1 inhibitor is selected from the following:

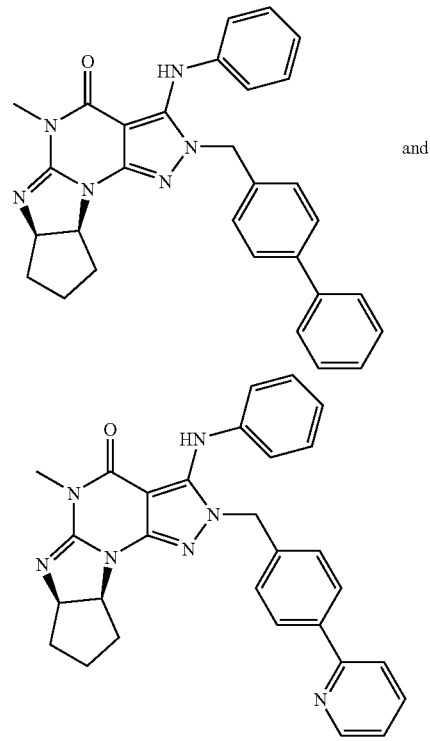

and in free or pharmaceutically acceptable salt form.

14. The method according to claim 13, wherein said patient is also suffering from a physiological disorder, symptom or disease selected from a group consisting of exercise amenorrhoea, anovulation, menopause, menopausal symptoms, hypothyroidism, pre-menstrual syndrome, premature labor, infertility, irregular menstrual cycles, abnormal uterine bleeding, osteoporosis, autoimmune disease, multiple sclerosis, estrogen-induced endometrial hyperplasia and estrogen-induced endometrial carcinoma.

15. The method according to claim 13, wherein said patient is a human.

* * * * *